(12) United States Patent
Anderson

(10) Patent No.: US 9,629,435 B2
(45) Date of Patent: Apr. 25, 2017

(54) COMBINATION HAIR WRAP, SLEEP MASK, AND READING LIGHT

(71) Applicant: Antonio Anderson, Conyers, GA (US)

(72) Inventor: Antonio Anderson, Conyers, GA (US)

( * ) Notice: Subject to any disclaimer, the term of this patent is extended or adjusted under 35 U.S.C. 154(b) by 821 days.

(21) Appl. No.: 13/928,193

(22) Filed: Jun. 26, 2013

(65) Prior Publication Data

US 2015/0000006 A1     Jan. 1, 2015

(51) Int. Cl.
| A45D 8/36 | (2006.01) |
|---|---|
| A61F 9/04 | (2006.01) |
| A45D 8/00 | (2006.01) |
| A45F 5/00 | (2006.01) |

(52) U.S. Cl.
CPC .............. *A45D 8/00* (2013.01); *A45D 8/36* (2013.01); *A45F 2005/002* (2013.01); *A61F 9/04* (2013.01)

(58) Field of Classification Search
CPC ....... A45D 8/00; A45D 8/36; A45F 2005/002; A61F 9/04; A61F 9/045; A42B 1/06; A42B 1/061; A42B 1/24; A42B 1/242; A42B 1/244
USPC ..................... 2/173, 202, 206, 207
See application file for complete search history.

(56) References Cited

U.S. PATENT DOCUMENTS

| 945,839 | A | * | 1/1910 | Brisbane | A61F 13/124 2/15 |
|---|---|---|---|---|---|
| 1,650,258 | A | * | 11/1927 | Bloomfield | A42B 1/066 2/172 |
| 1,807,475 | A | * | 5/1931 | Gibson | A61F 9/04 2/15 |
| 3,541,608 | A | * | 11/1970 | Otwell | A61F 9/04 128/DIG. 15 |
| 3,555,565 | A | * | 1/1971 | Zimmon et al. | A42B 1/043 2/195.7 |
| 3,780,379 | A | * | 12/1973 | Kampman | A61F 13/124 2/15 |
| 4,254,451 | A | * | 3/1981 | Cochran, Jr. | A44C 15/0015 315/323 |
| 4,644,588 | A | * | 2/1987 | Zawacki | A61F 9/04 128/858 |
| 4,821,341 | A | * | 4/1989 | Baptiste | A42B 1/062 2/10 |
| 5,067,174 | A | * | 11/1991 | Ritchey | A41D 13/11 128/201.17 |
| 5,123,116 | A | * | 6/1992 | Roth | A63B 69/004 2/15 |
| 5,667,292 | A | * | 9/1997 | Sabalvaro, Jr. | A42B 1/244 2/10 |
| 5,676,449 | A | * | 10/1997 | Newsome | A42B 1/244 362/105 |
| 5,845,340 | A | * | 12/1998 | Frislie | A41D 13/1153 2/173 |
| 6,088,836 | A | * | 7/2000 | de Cordova | A47C 7/383 2/15 |
| 6,168,286 | B1 | * | 1/2001 | Duffy | A42B 1/242 362/105 |

(Continued)

*Primary Examiner* — Alissa L Hoey
(74) *Attorney, Agent, or Firm* — Laurence P. Colton; Smith Tempel Blaha LLC

(57) ABSTRACT

A headgear device having a hair wrap component for maintaining at least a portion of a user's hair in a desired position, an eye mask component for covering a user's eyes, the eye mask component being movable from a lowered position for covering a user's eyes to a raised position for not covering a user's eyes, and a light component.

3 Claims, 32 Drawing Sheets

(56) References Cited

U.S. PATENT DOCUMENTS

| | | | | |
|---|---|---|---|---|
| 6,397,395 B1 * | 6/2002 | DeHart | A41D 3/005 | 2/173 |
| 6,612,695 B2 * | 9/2003 | Waters | F21V 21/084 | 351/158 |
| 6,721,962 B1 * | 4/2004 | Polaire | A42B 1/244 | 2/209.13 |
| 6,733,150 B1 * | 5/2004 | Hanley | A42B 1/244 | 2/209.13 |
| 6,758,215 B2 * | 7/2004 | Begum | A41D 13/1161 | 128/202.15 |
| 6,935,761 B2 * | 8/2005 | Vanderschuit | A42B 1/062 | 362/106 |
| 6,994,445 B1 * | 2/2006 | Pomes | A42B 1/244 | 2/209.13 |
| 7,000,841 B2 * | 2/2006 | Becker | F21V 21/084 | 2/10 |
| 7,131,148 B1 * | 11/2006 | Traumer | A42B 1/041 | 2/10 |
| 7,234,831 B1 * | 6/2007 | Hanley | A42B 1/244 | 2/209.13 |
| 7,268,669 B2 * | 9/2007 | McEvoy | A61F 11/14 | 340/309.16 |
| 7,427,149 B2 * | 9/2008 | Sohn | F21S 9/037 | 362/106 |
| 7,506,992 B2 * | 3/2009 | Carter | F21L 4/00 | 2/209.13 |
| 7,566,139 B1 * | 7/2009 | Dority | F21V 21/084 | 362/103 |
| 7,690,052 B2 * | 4/2010 | Saladino | A42B 1/247 | 2/10 |
| 7,784,960 B2 * | 8/2010 | Lahtinen | A42B 1/244 | 362/105 |
| 8,002,437 B2 * | 8/2011 | Sohn | A42B 1/244 | 362/249.01 |
| 8,444,266 B2 * | 5/2013 | Waters | G02C 5/146 | 351/158 |
| 8,621,668 B1 * | 1/2014 | Nolz | A42B 5/00 | 2/171.4 |
| 8,794,242 B1 * | 8/2014 | Kroening | A61F 9/04 | 128/857 |
| 8,813,268 B1 * | 8/2014 | Fitzgerald | A42B 1/242 | 2/422 |
| 2006/0007671 A1 * | 1/2006 | Lavoie | G02C 11/04 | 362/103 |
| 2006/0198122 A1 * | 9/2006 | Senter | A42B 3/044 | 362/105 |
| 2007/0159807 A1 * | 7/2007 | Pereira | A42B 1/244 | 362/102 |
| 2010/0095977 A1 * | 4/2010 | Schmitz | A45D 8/36 | 132/275 |
| 2010/0186145 A1 * | 7/2010 | Macy | A42B 1/061 | 2/207 |
| 2010/0229275 A1 * | 9/2010 | Wilson | A61F 9/04 | 2/15 |
| 2011/0271421 A1 * | 11/2011 | Vahey | A42B 1/061 | 2/173 |
| 2012/0131726 A1 * | 5/2012 | Schenk | A61F 9/04 | 2/173 |
| 2012/0137406 A1 * | 6/2012 | Hide | A61F 9/04 | 2/206 |
| 2013/0060306 A1 * | 3/2013 | Colbauch | A61N 5/0618 | 607/88 |
| 2014/0009282 A1 * | 1/2014 | Baloa Welzien | G04G 11/00 | 340/539.11 |
| 2014/0049947 A1 * | 2/2014 | Lombard | A41D 19/0157 | 362/106 |
| 2014/0053318 A1 * | 2/2014 | Fitzgerald | A42B 1/006 | 2/209.13 |
| 2014/0268683 A1 * | 9/2014 | Waters | A42B 1/244 | 362/106 |
| 2015/0092972 A1 * | 4/2015 | Lai | H04R 1/1008 | 381/333 |

* cited by examiner

US 9,629,435 B2

COMBINATION HAIR WRAP, SLEEP MASK, AND READING LIGHT

BACKGROUND OF THE INVENTION

Technical Field

This invention relates generally to the field of hair care and convenience in maintaining hair styles, and relates more specifically to the field of devices for hair care and convenience in maintaining hair styles while conducting other activities.

Prior Art

The hair care and styling field is rife with implements and devices for maintaining hair styles. Such devices and implements range from a simple hair wrap to maintain a hair style while engaged in other activities to more complex devices for accomplishing the same purpose.

BRIEF SUMMARY OF THE INVENTION

Briefly, the present invention is a hair wrap or scarf, generally referred to by the inventor as head hair gear, which is designed for women and men when they are preparing to go to sleep. The current devices that are on the market are simple hair wraps, scarves, or wave caps that are used to keep the hair in a secured manner while an individual is preparing to sleep. The current devices on the market are designed for one thing only and have only one working method, which is to keep styled or rolled hair in place and prepared for morning styling.

The new device and method of the present invention is a multifunctional apparatus that incorporates a sleep mask and a reading light custom built into any night time cloth or fabric flexible material. The hair wrap, eye mask, reading light combination of the present invention works in the following manner. The hair wrap component and the eye mask component are both products designed if an individual is resting or fully going to bed. However, the eye mask component can be lowered from a raised position in the hair wrap material to a lowered position in which it is an eye mask for total sleep comfort. If an individual decides not to use the eye mask component, this component can be fully raised and integrated back into the wrap fabric material, and even can be placed in a hidden configuration so as to be generally unnoticeable.

Moreover, if an individual decides they want to use the light component, which has many separate benefits, the individual can flip up the eye mask component. A hook and loop fastener material, or other fastening means, can be used to secure the eye mask component in place. The light component is built in the eye mask component, generally in the middle of the eye mask component. The light component is useful if, for example, a person wants to use the light component for reading in bed before going to sleep. A push button on-off switch is provided for activating the light, and the user can simply push the button to turn on the light, illuminating any type of reading material desired.

An embodiment of the light component comprises of one or more light emitting diodes (LED), wiring between the light and the switch, and a battery. The wiring preferably is hidden in the fabric of the wrap material so as to be hidden from view. Also, additional wiring connects the battery to the switch and light. The battery can be located in a switch housing, in a light housing, or on the inside of the wrap fabric. The light has many functions, such as but not limited to, illuminating a dark room, providing light for nursing a baby in a low lit room, perhaps taking a late evening walk to get attention of traveling cars, and, of course, illuminating a book for reading.

A preferred embodiment of the wire, battery and switch components, alone or in various convenient combinations, sits in one or more waterproof plastic pouches, with, if necessary, waterproof connections between these components and with the light component. This allows the user to wash the wrap material component separate from the eye mask component, as the battery and switch components can be located in the wrap material, while the light component can be located in the eye mask component, which can be separated from the wrap material. For example, the eye mask can be designed to disconnect from the base of the hair wrap using simple hook and loop material, or other connecting means. After washing the wrap material, the wrap material can be fully assembled back to the eye mask component. Alternatively, the eye mask component can be non-detachable from the wrap material and just be a total part of the wrap fabric component, and can just be lowered down without using any type of connection means.

As alternative, the eye mask component can be replaced with an eye shade component. In such an alternative embodiment, the eye mask component can be removed from the hair wrap and replaced with the eye shade when traveling outside the house where sun will be present. Thus, the inventive device also can include a daytime feature when the user desires to protect a hair style during the day, and will allow the user the ability to leave traditional eye shades or visors at home. For example, the user can quickly remove the eye mask and replace it with the eye shade for traveling, and then remove the eye shade and replace it with the eye mask if the user wants to get some sleep, perhaps on an airplane during traveling.

BRIEF DESCRIPTION OF THE DRAWINGS

FIG. 16 is a view of a user wearing the invention with the eye mask raised and turning the light on.

DETAILED DESCRIPTION OF PREFERRED EMBODIMENTS

Referring now to the figures, the device 10 and method of the present invention is a multifunctional apparatus that incorporates a eye mask 14 for sleeping and a reading light 16 for providing illumination custom built into any night time cloth or fabric flexible hair wrap 12 material. The eye mask 14 can be lowered from a raised position in the hair wrap 12 material to a lowered position in which it provides for darkness for sleep comfort. If a user U decides not to use the eye mask 14, the eye mask 14 can be fully raised and integrated back into the hair wrap 12 material, and even can be placed in a hidden configuration so as to be generally unnoticeable.

Figure 1:
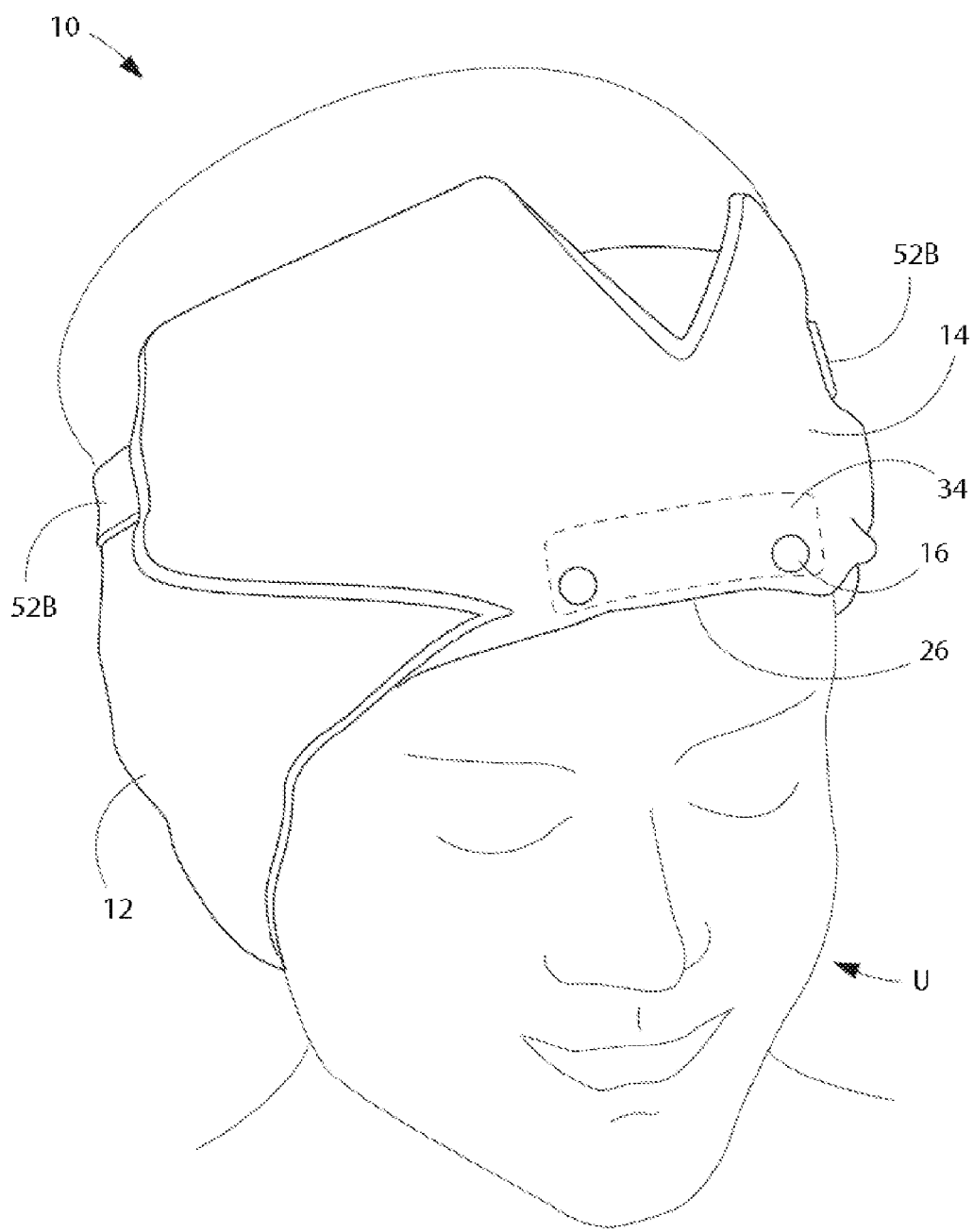
FIG. 1 is a side perspective view of an embodiment of the present invention shown on the head of a user in a position with the eye mask in a raised position and the lights uncovered.
Figure 2:
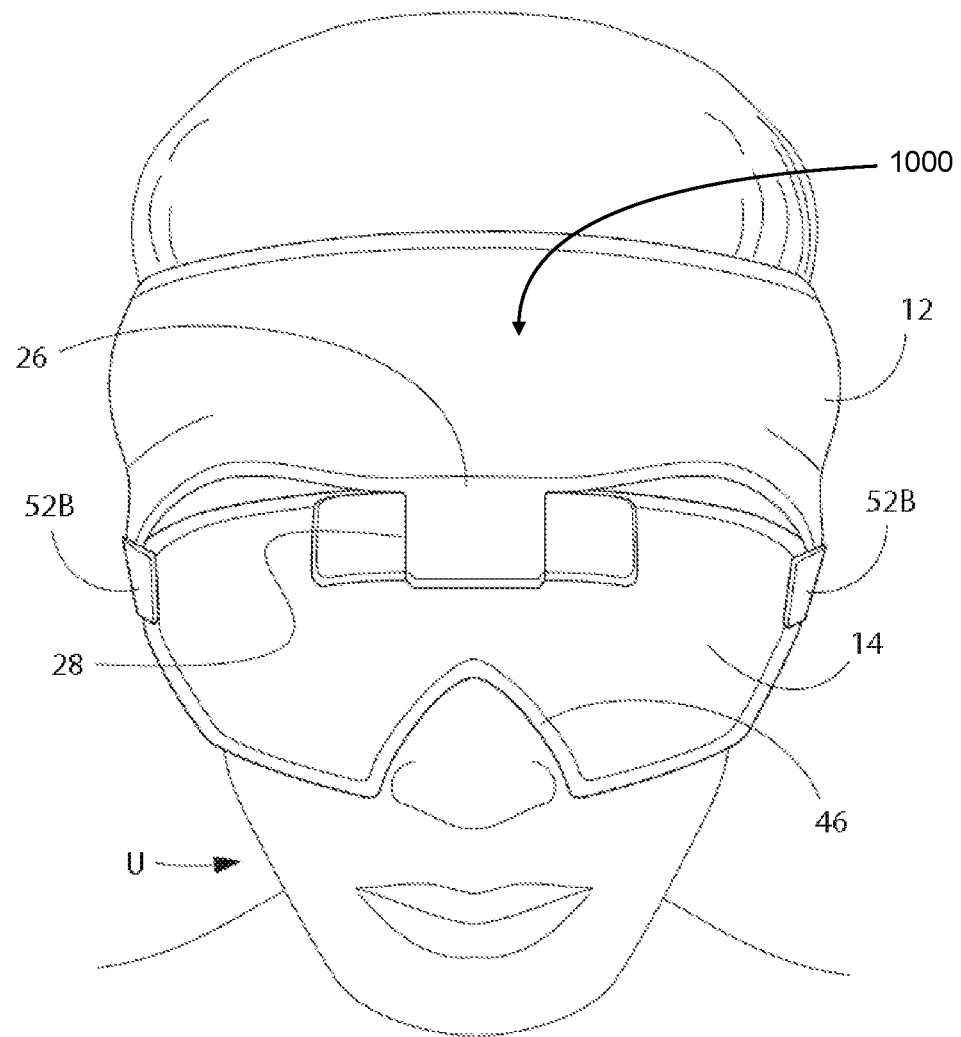
FIG. 2 is a front view of the embodiment of FIG. 1 shown in a position with the eye mask in a lowered position.
Figure 3:
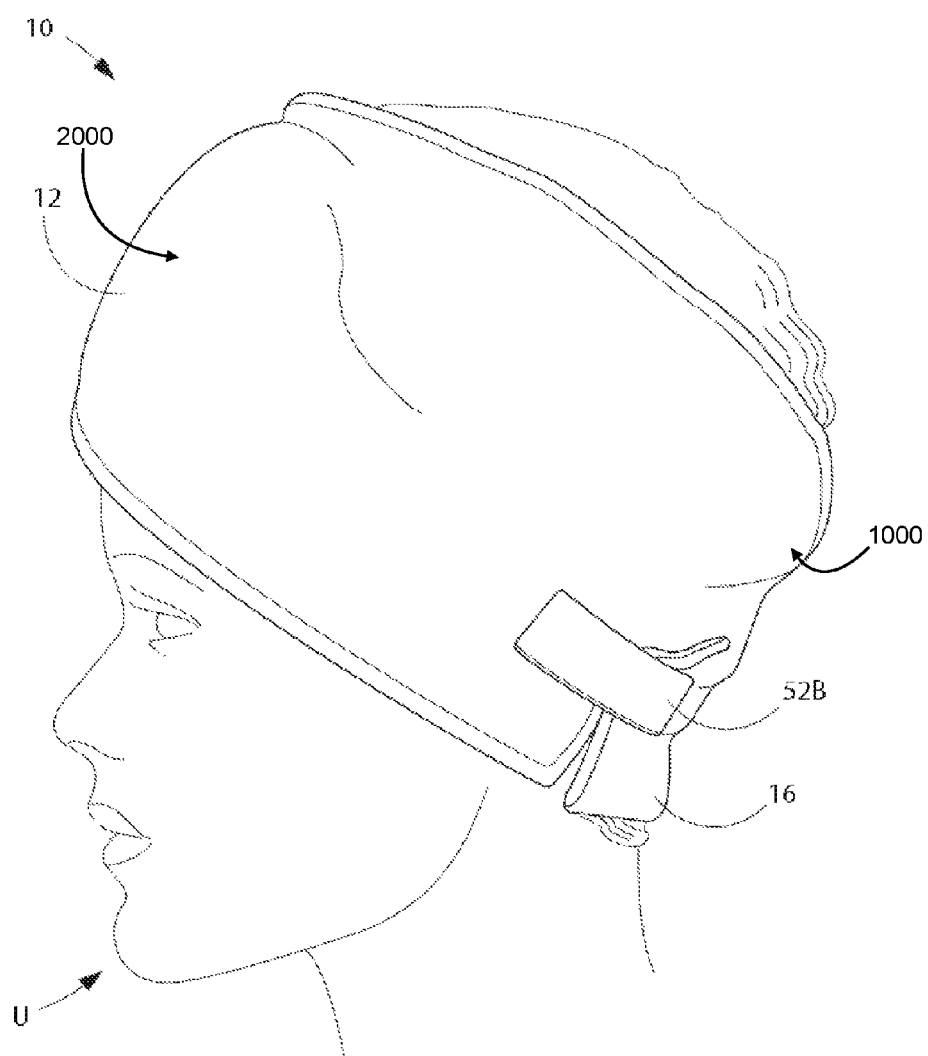
FIG. 3 is a side perspective view of the embodiment of FIG. 1 shown with the eye mask at the back of the head.

Referring now to FIGS. 1 through 3, these figures show perspective views of an embodiment of the present device 10, which is a combination hair wrap 12, eye mask 14, and reading light 16, shown on the head of a user U. FIG. 1 is a front perspective view of the device 10 shown with the eye mask 14 in a raised position and the reading light 16 uncovered, FIG. 2 is a front view of the device 10 shown with the eye mask 14 in a lowered position, and FIG. 3 is a side perspective view of the device 10 shown with the eye mask 14 at the back of the head.

The device 10 comprises a sheet of material 18 as the hair wrap 12, which can be in many alternative forms. In FIGS. 1 through 3, the sheet of material 18 is in the form of a headband covering the sides of the user's U head, including generally the user's ears, forehead, and back of the head, but leaving the crown of the head uncovered. The headband/hair wrap 12 has a front section 1000 and rear section 2000 antipodal to the front section 1000. In the exemplary embodiment of FIGS. 1 through 3, the front section 1000 has a smaller band width than the rear section 2000. The hair wrap 12 can be wrapped around the head, or drawn over the top of the head, to cover and secure the user's U hair, thereby preventing the user's U hair from becoming disheveled, and thereby positioning the tapered front section 1000 to contour about the user's face. This is particularly useful in protecting a hair style from being ruined when, for example, sleeping or being out in windy conditions.

FIG. 1 shows a representative eye mask 14 attached to the hair wrap 12, and reading lights 16 mounted on the eye mask 14. Also can be seen in outline is the light unit 34 located within the interior of the eye mask 14. Holes 44 through the eye mask 14 allow the reading lights 16 to shine where desired. Eye mask 14 is located in the raised position, in which position the user's U eyes are not covered and the reading lights 16 can illuminate a desired area. This is the position generally preferred when the user U is awake and doing other tasks.

FIG. 2 shows the eye mask 14 in the lowered position, in which the user's U eyes are covered and the reading lights 16 are hidden. This is the position generally preferred when the user is asleep or trying to fall asleep. Eye mask 14 is attached to hair wrap 12 by hinge 26 for allowing the eye mask 14 to be moved between the raised position and the lowered position. In this embodiment, the movement of eye mask 14 relative to hair wrap 12 is generally a folding motion upwards to raise the eye mask 14 and downwards to lower the eye mask 14. The hinge may be a fabric connection between eye mask 14 and hair wrap 12 in which eye mask 14 is a part of the same piece of material as hair wrap 12. Alternatively, the hinge 26 also may be or may include a connector 28 so that the eye mask 14 can be disconnected and removed from the hair wrap 12, in which embodiment the eye mask 14 is a separate piece of material from hair wrap 12. Eye mask 14 may include a nose cutout 46 for comfort FIG. 3 shows the device 10 on a user's head in a position rotated approximately 180 degrees from that shown in FIGS. 1 and 2, in which the eye mask 14 is located at the back of the user's U head. A user U may want to use the device 10 in this position when there is no desire to use the eye mask 14 and the user U prefers a smooth looking frontal presentation. The eye mask 14 is in the lowered position in this figure. The hair wrap 12 can be wrapped around the head, or drawn over the top of the head, to cover and secure the user's U hair, thereby positioning the tapered front section 1000 to contour about the user's neck.

Figure 4:
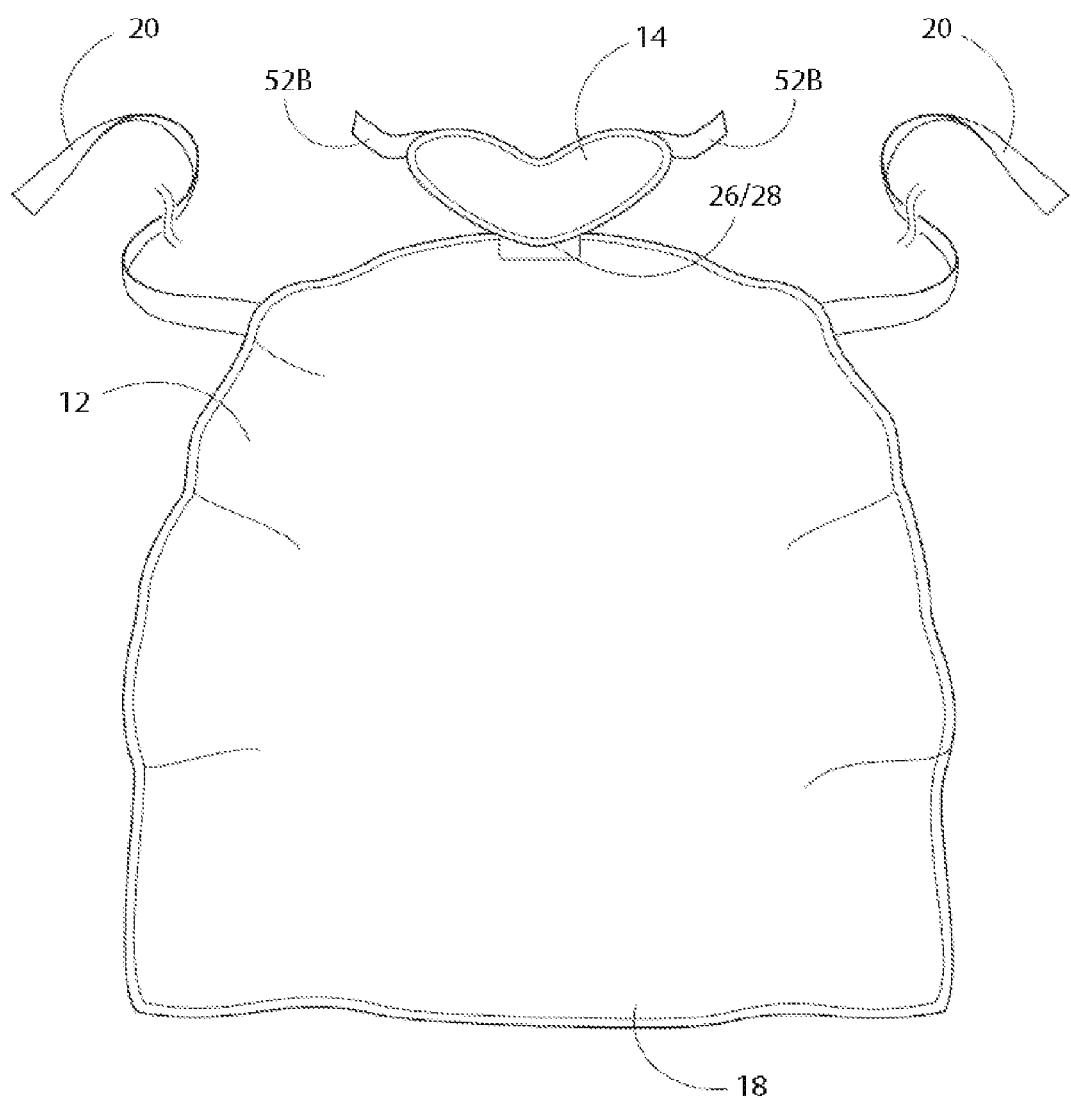
FIG. 4 is a perspective view of an embodiment of the invention shown in a disassembled state.

Referring now to FIG. 4, this figure is a perspective view of an embodiment of the device 10 shown in the form of a sheet of material 18 in a disassembled state. In this embodiment, rather than in the form of a head band, the hair wrap 12 is in the form of a scarf or bandana that can be placed over the entire head, and therefore covers the top of the head and a majority or all of the user's U hair. The sheet of material 18 can be wrapped about the user's U hair when in use, using ties 20 to secure the device on the user's U head. Eye mask 14 is shown depending from the sheet of material 18.

Figure 5:
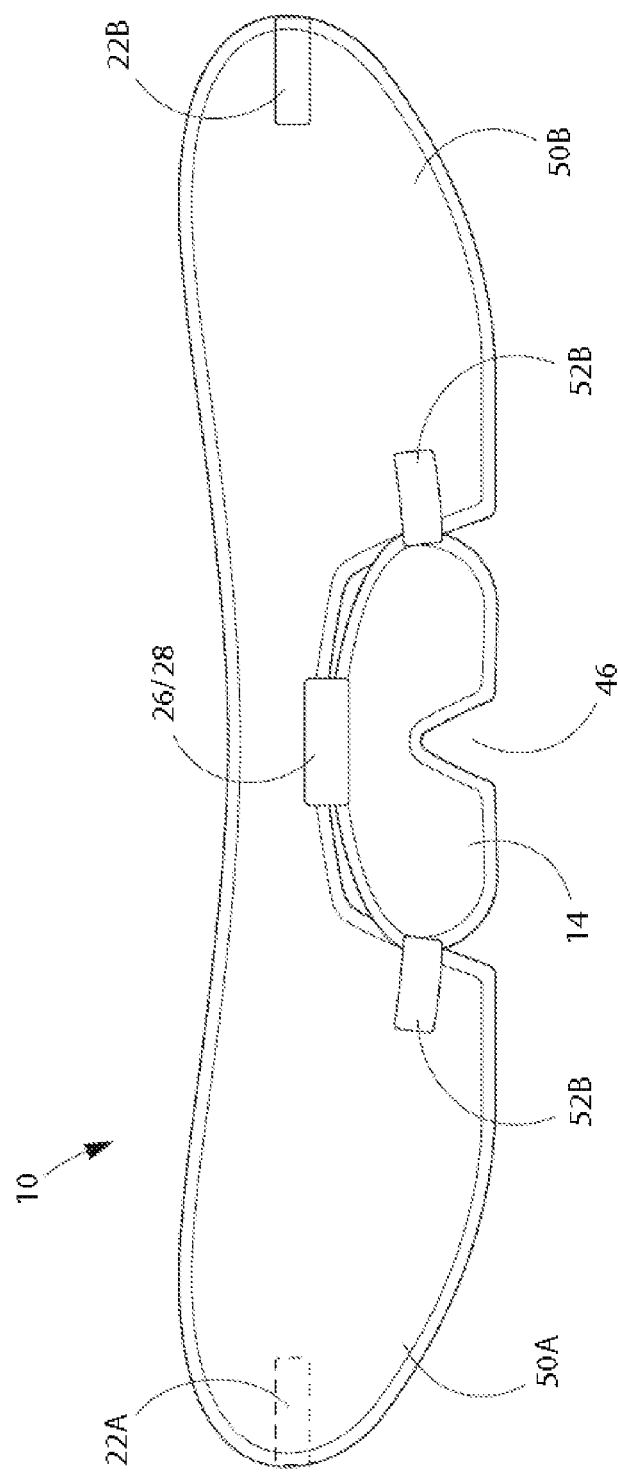
FIG. 5 is a front view of a first embodiment of the invention with an eye mask component of the present invention shown in the lowered position.
Figure 6:
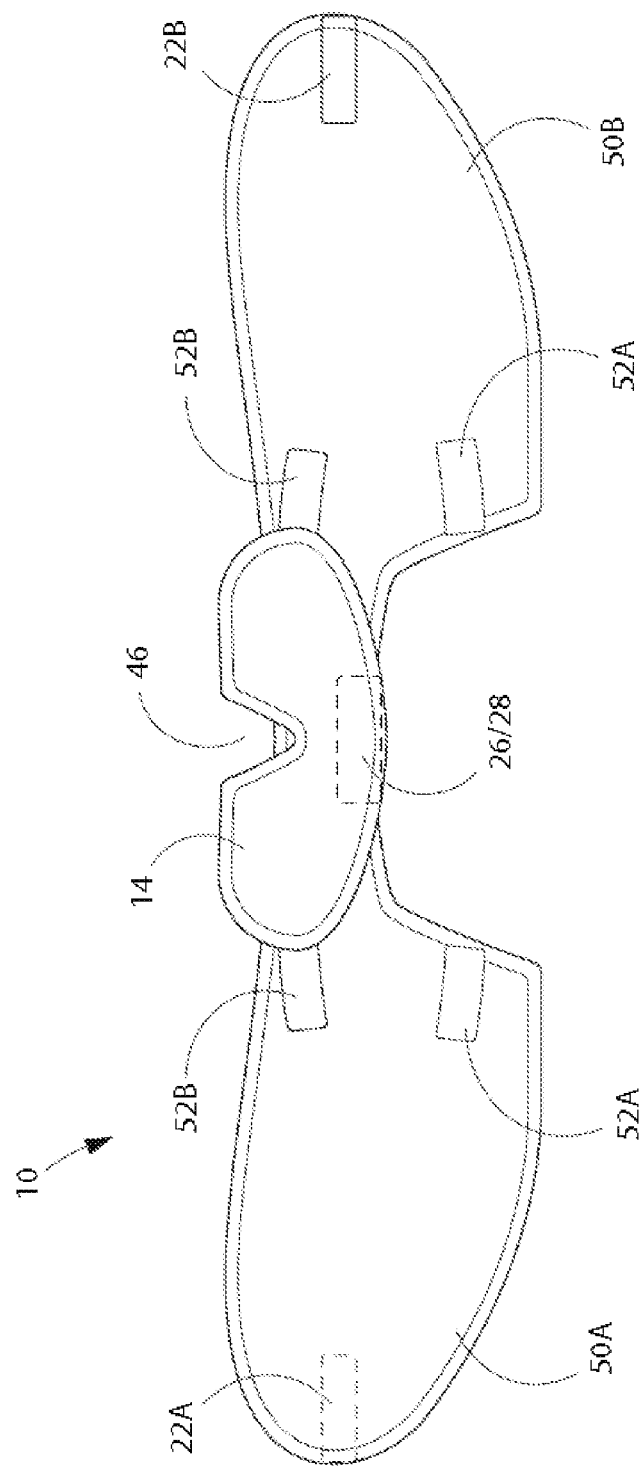
FIG. 6 is a front view of the embodiment of FIG. 5 with an eye mask shown in the raised position.

Referring now to FIGS. 5 and 6, these figures are front views of a first embodiment of the device 10. FIG. 5 shows the eye mask 14 in the unfolded, lowered position for use when sleeping and FIG. 6 shows the eye mask 14 in the folded, raised position for use when awake. In this embodiment, the device generally comprises two sections, the hair wrap 12 generally in the form of a headband and the eye mask 14. The hair wrap 12 is an elongated oval having two arms 50A, 50B, with the eye mask 14 attached generally in a recess in the middle of the oval. On either end of the oval are connection means 22A, 22B to secure the two ends of the two arms 50A, 50B of the hair wrap 12 to each other when secured on the user's U head. For example, hook and loop fastener, snaps, clips, and the like can be used as the connection means 22A, 22B.

In one use of the device 10 of FIGS. 5 and 6, the user U places the center of the oval at the user's U forehead, and wraps the two arms 50A, 50B about either side of the user's U head, and connects the ends of the two arms 50A, 50b, and specifically the connection means 22A, 22B, together at the back of the user's U head. This secures the device 10 about the circumference of the user's U head with the eye mask 14 located proximal to the user's U eyes, that is on the user's U forehead above the user's U eyes when the eye mask 14 is in the raised position. The eye mask 14 then can be raised and lowered to uncover or cover, respectively, the user's U eyes.

In another use of the device 10 of FIGS. 5 and 6, the user U places the center of the oval at the back of the user's U head, and wraps the two arms 50A, 50B about either side of the user's U head, and connects the ends of the two arms 50A, 50b, and specifically the connection means 22A, 22B, together at the front of the user's U head, namely, at the user's U forehead. This secures the device 10 about the circumference of the user's U head with the eye mask 14 located proximal to the back of the user's U head. The eye mask 14 is not used in this use, but can be used as additional support or protection for the hair style at the back of the user's U head.

Figure 7:
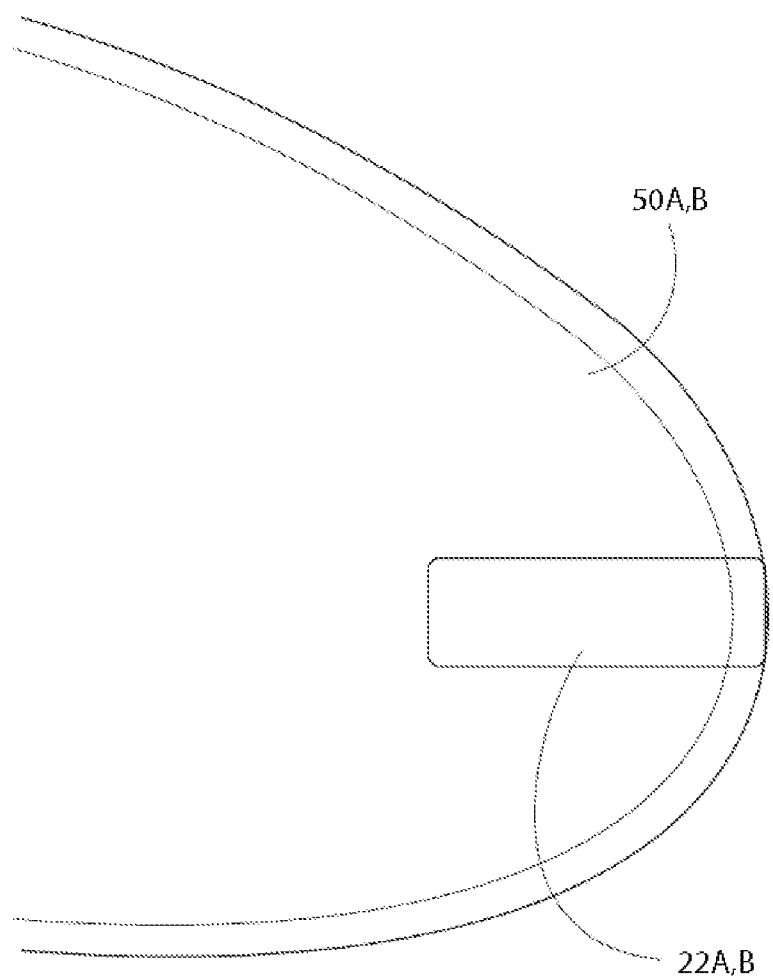
FIG. 7 is a side view of the invention showing a connection means for holding the eye mask in a desired position.

Referring now to FIG. 7, this figure is a side view of the arm 50A or 50B of the hair wrap 12 of FIGS. 5 and 6 showing one part of the connection means 22A or 22B for securing the hair wrap about the user's U head. In this embodiment, the connection means 22A or 22B is a first half of a hook and loop fastener material. Other known and future developed connection means can be used with the device 10.

Figure 8:
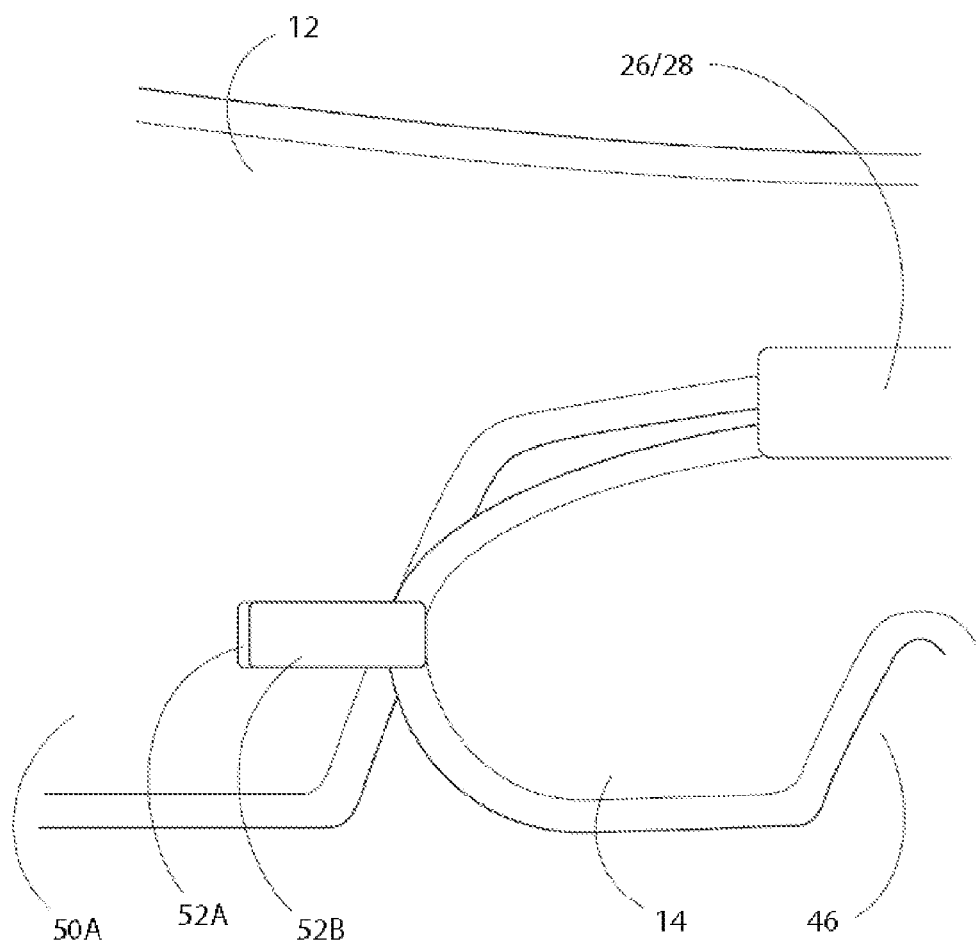
FIG. 8 is a side view of a means for securing the eye mask in position on the hair wrap.

Referring now to FIG. 8, this figure is a side view of a means for securing the eye mask 14 in position on the hair wrap 12. Part of arm 50A is shown along with the eye mask 14 and securing means 52A, 52B. First part of securing means 52A can be located on the arm 50A and second part of securing means 52B can be located on the eye mask 14, or vice versa. Eye mask 14 is in the lowered position and one end 54A of eye mask 14 is shown secured to arm 50A by a hook and look fastener. Securing means 52A, 52B can be and preferably is located on arm 50A in a position such that when eye mask 14 is either in the lowered or raised position, second part of securing means 52B can attach to first part of securing means 52A so as to secure the eye mask 14 in the desired lowered or raised position.

Figure 9:
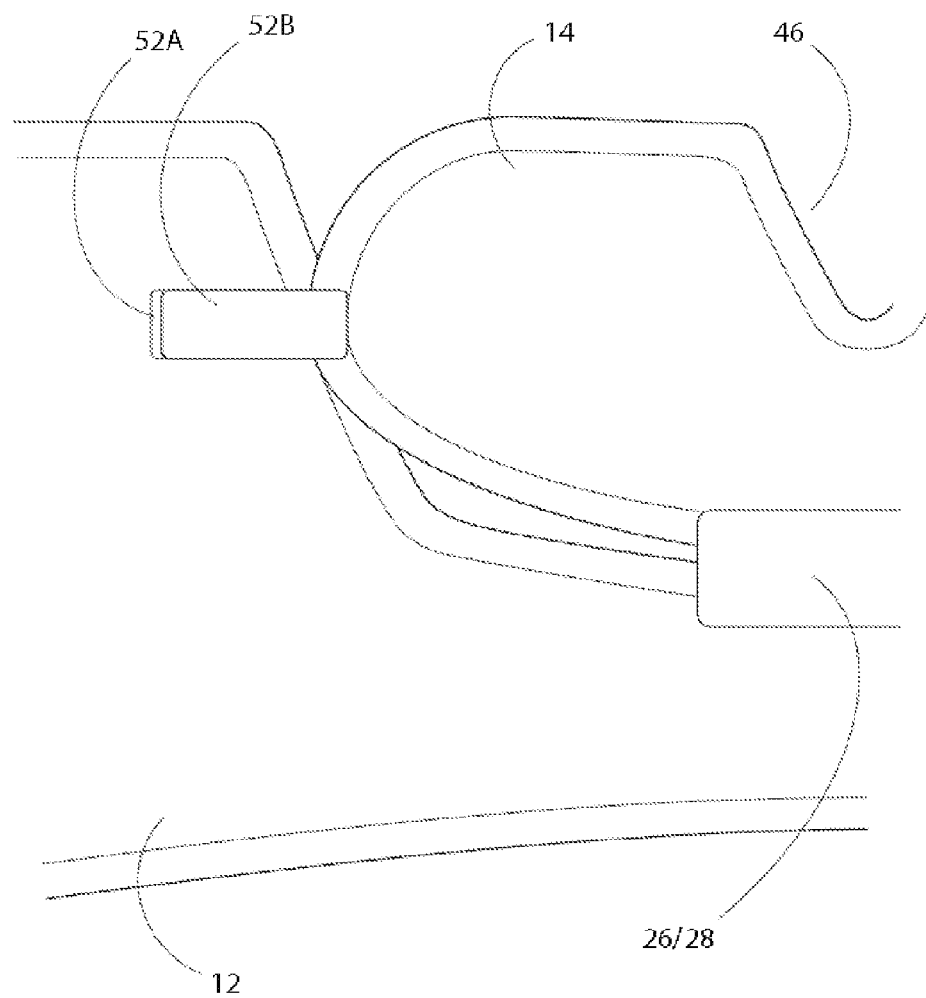
FIG. 9 is a side view of a connection means for holding the eye mask in a desired position.

Referring now to FIG. 9, this figure is a side view of the eye mask 14 connected to the hair wrap 12 and showing a second part of securing means 52B for holding the eye mask 14 to the hair wrap 12. In this embodiment, the second part of securing means 52B is a second half of a hook and loop fastener material.

Figure 10:
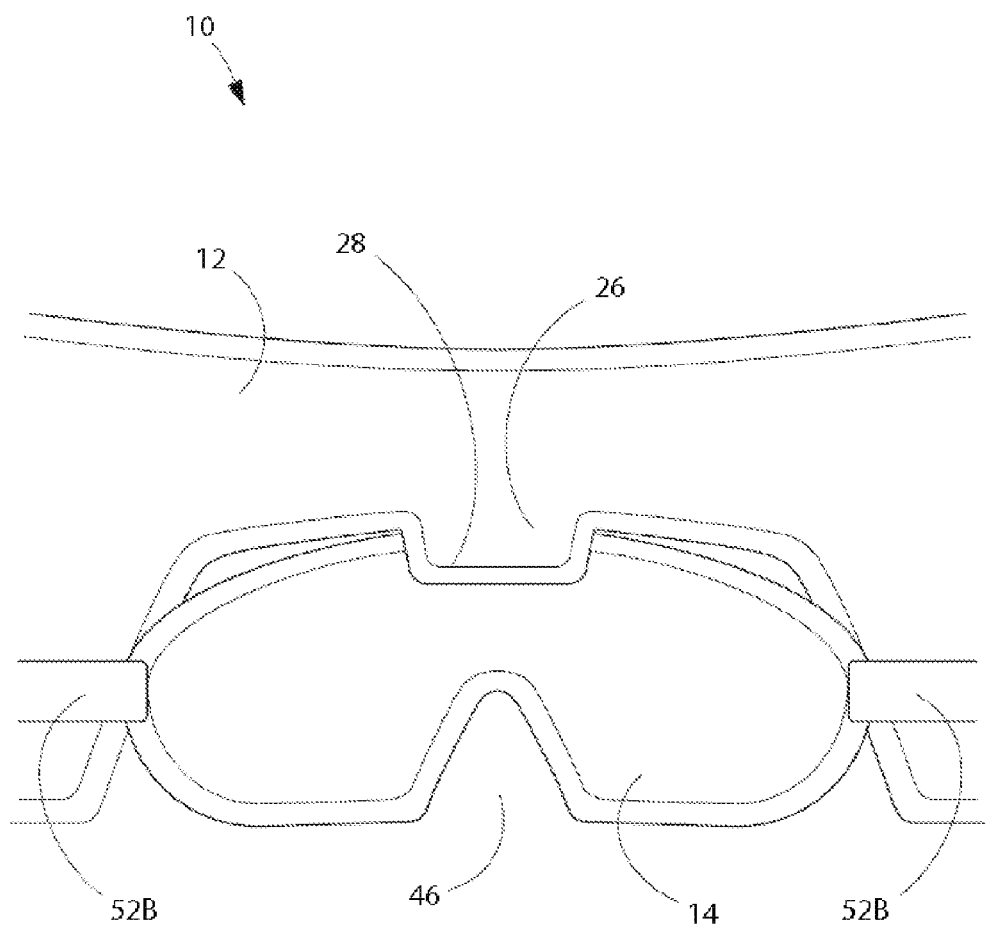
FIG. 10 is a front view of an eye mask component of the present invention in the lowered position in greater detail showing a hinge for allowing the eye mask to be moved between the raised position and the lowered position.

Referring now to FIG. 10, this figure is a front view of an eye mask 14 of the device 10 in the lowered position in greater detail showing a hinge 26 for allowing the eye mask 14 to be moved between the raised position and the lowered position. The hinge 26 also may be or may include a connector 28 so that the eye mask 14 can be disconnected and removed from the hair wrap 12.

Figure 11:
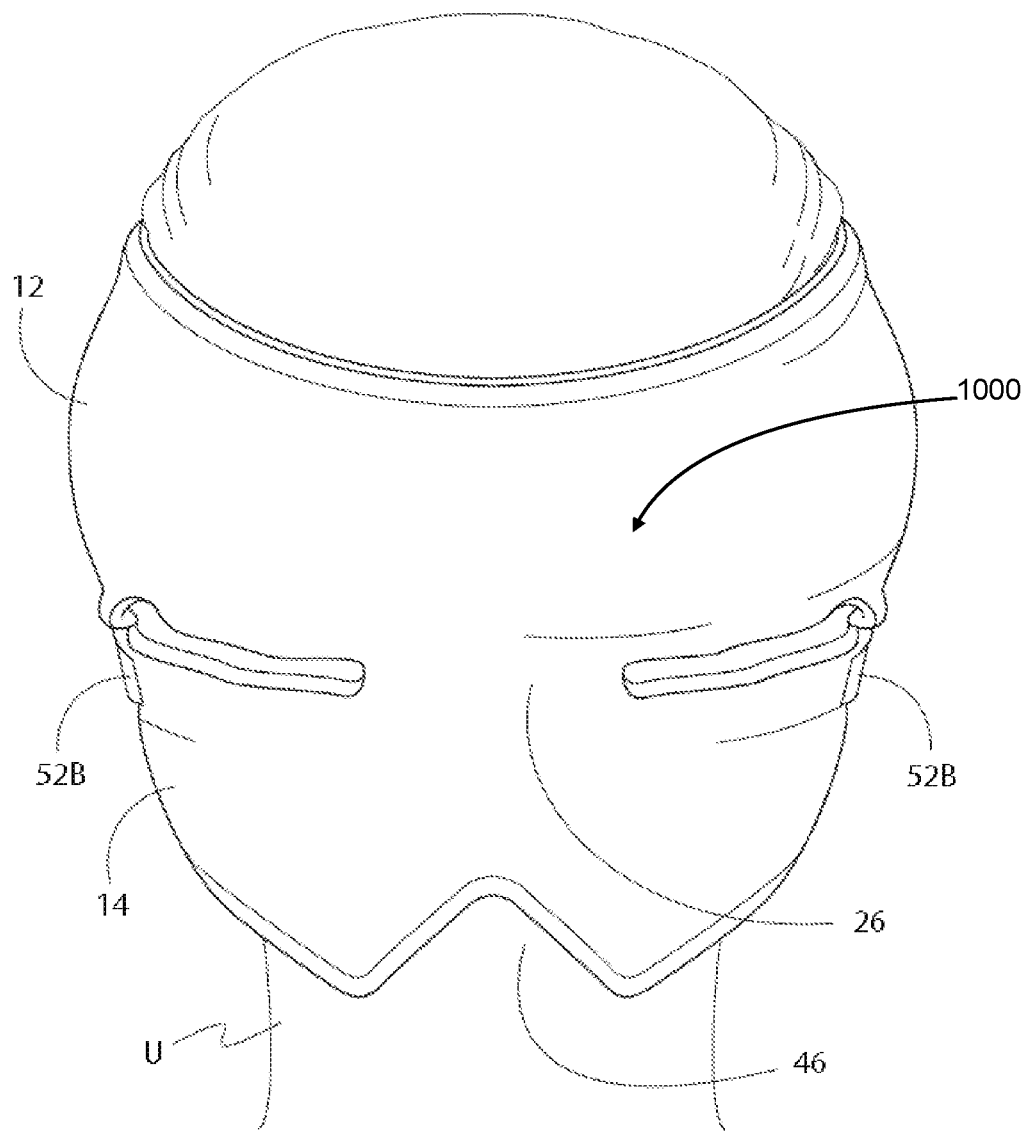
FIG. 11 is a view of the embodiment of FIG. 1 shown worn on a user in an alternative manner.
Figure 12:
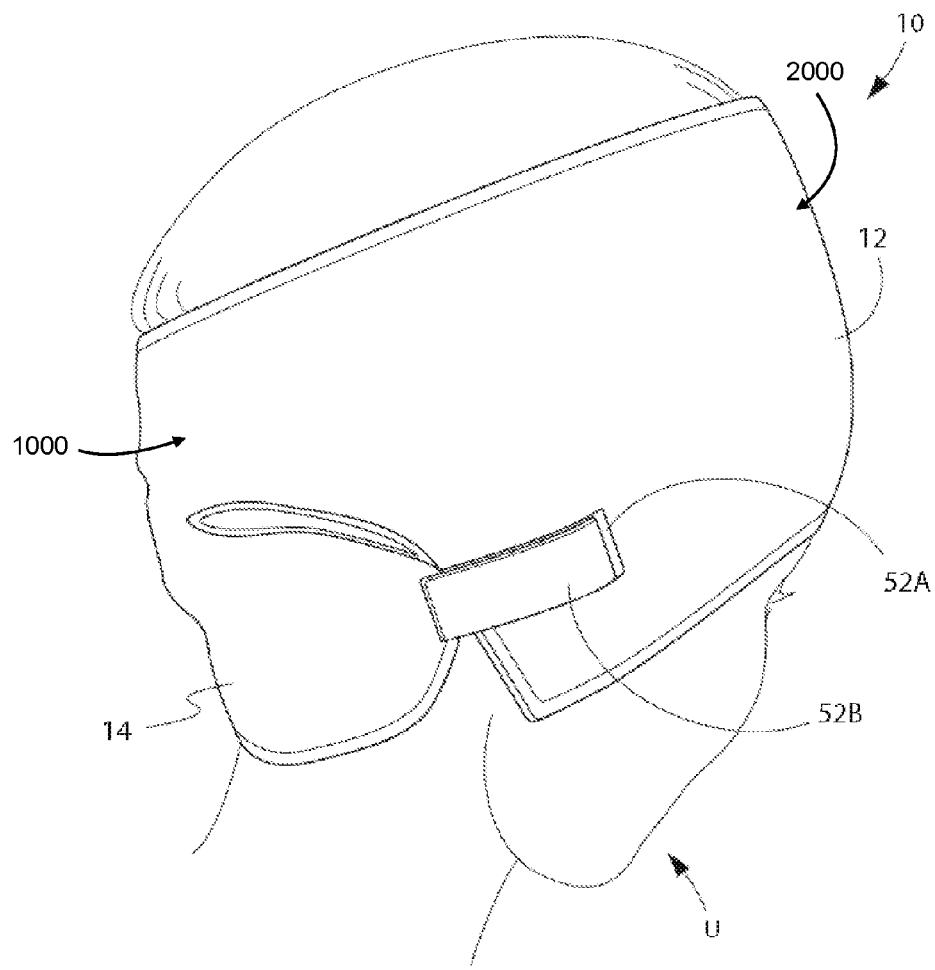
FIG. 12 is a rear perspective view of the embodiment of FIG. 1 showing the means for adjusting the fit of the invention on the user in greater detail.

Referring now to FIGS. 11 and 12, these figures are views of the device 10 shown worn by a user U in an alternative manner. In these views, the user U is wearing the device 10 with the eye mask 14 located on the back of the user's U head. In other words, the device 10 is being worn backwards. A user U would wear the device in this manner if the user U had no desire to use the eye mask 14 or the reading light 16. The eye mask 14 is shown in the lowered position so as to give more support or protection to the user's U hair style at the back of the user's U head.

Figure 13:
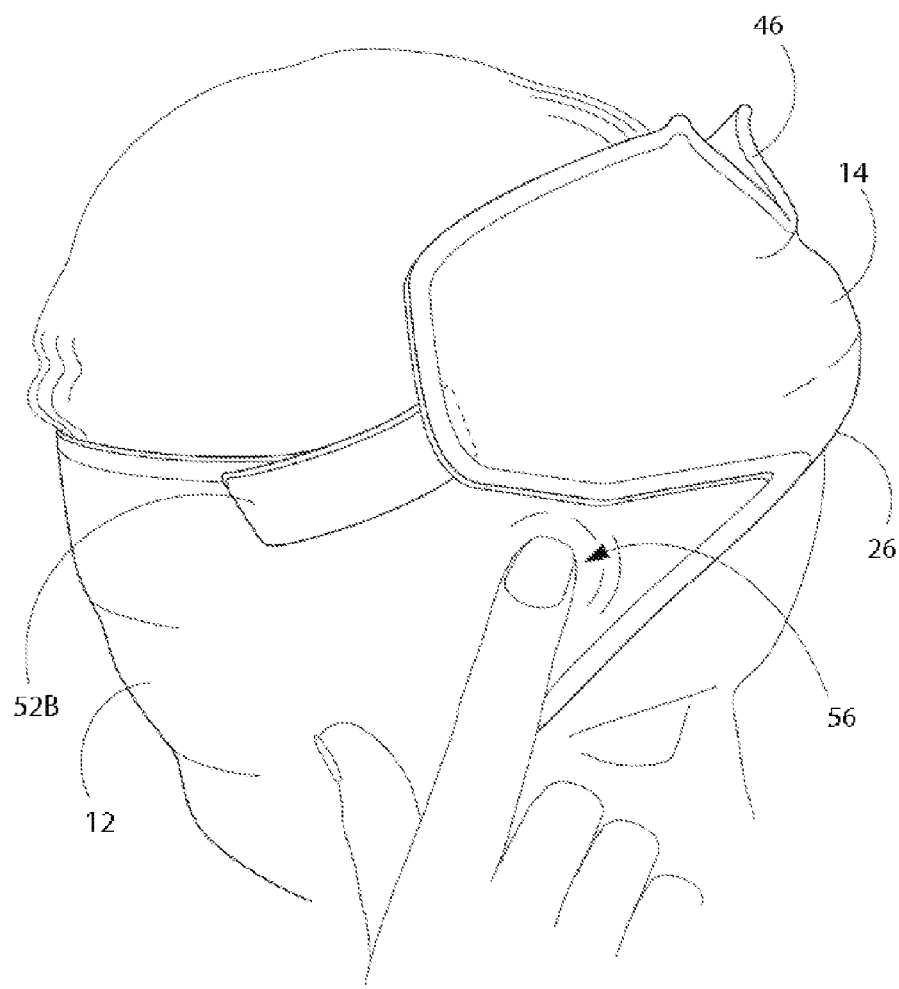
FIG. 13 is a side perspective view of the embodiment of FIG. 1 showing the eye mask in the raised position in greater detail.

Referring now to FIG. 13, this figure is a side perspective view of the device 10 showing the eye mask 14 in the raised position in greater detail. In this position, the reading lights 16 are exposed such that the reading lights 16 can illuminate, for example, a book. The user U is shown activating the on-off switch 30, which is contained within the hair wrap 12. More specifically, and as disclosed in more detail in connection with FIG. 14, the on-off switch unit 56 is located within the hair wrap 12 so that it is hidden from view. While the on-off switch unit 56 is shown located proximal to the user's U temple, the on-off switch unit 56 can be located at any position on or in the hair wrap 12, and even on the exterior of the hair wrap 12.

Figure 14:
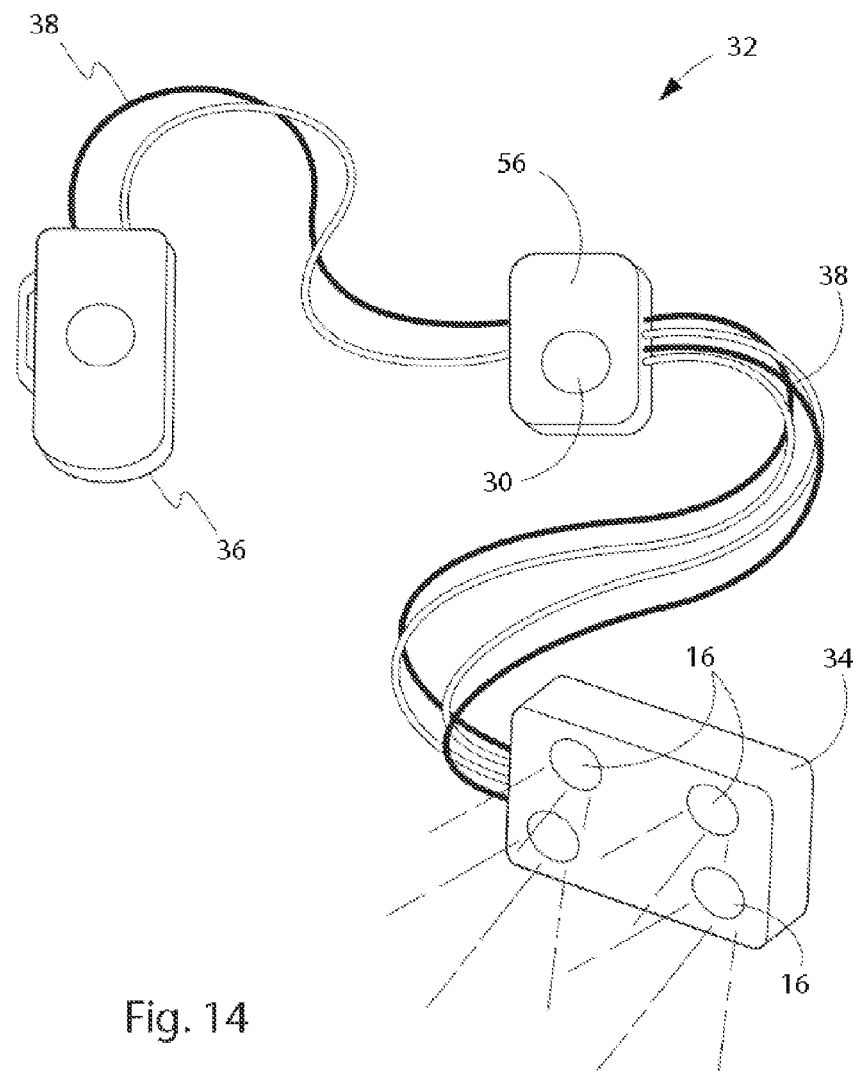
FIG. 14 is a plan view of a wiring harness for the present invention showing the light unit and the on-off switch unit.

Referring now to FIG. 14, this figure is a plan view of a wiring harness 32 for the device 10 showing the reading lights 16, the light unit 34, the on-off switch 30, the on-off switch unit 56, the battery unit 36 comprising a power source, and representative wiring 38 connecting the units 30, 34, 36 together. These components create a simple circuit between the reading lights 16, the battery unit 36, and the on-off switch 30. Light unit 34 comprises at least one reading light 16, and light unit 34 preferably is attached to and/or contained with the eye mask 14. Battery unit 36 comprises a battery (not shown) and preferably is attached to and/or contained within the hair wrap 12. On-off switch unit 56 comprises on-off switch 30, and on-off switch unit 56 preferably is attached to and/or located within the hair wrap 12. In use, the user U activates on-off switch 30 so as to activate the reading lights 16. Preferably, reading lights 16 are activated when the eye mask 14 is in the raised position.

Figure 15:
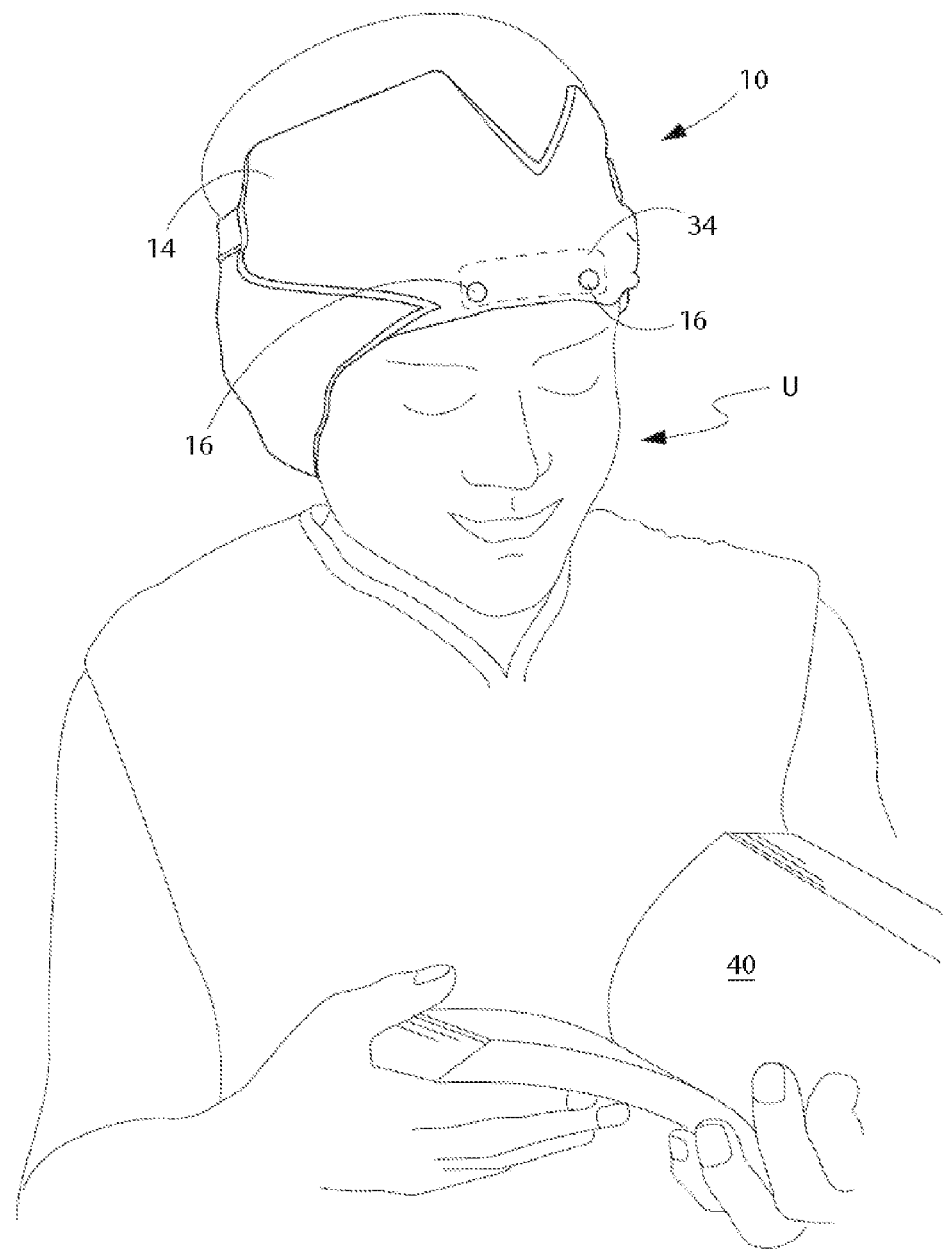
FIG. 15 is a view of a user wearing the invention with the eye mask raised and holding a book.

Referring now to FIGS. 15 through 19, these figures are views of the device 10 in operation. FIG. 15 is a view of a user U wearing the device 10 with the eye mask 14 raised and trying to read a book 40 in the dark.

Figure 16:
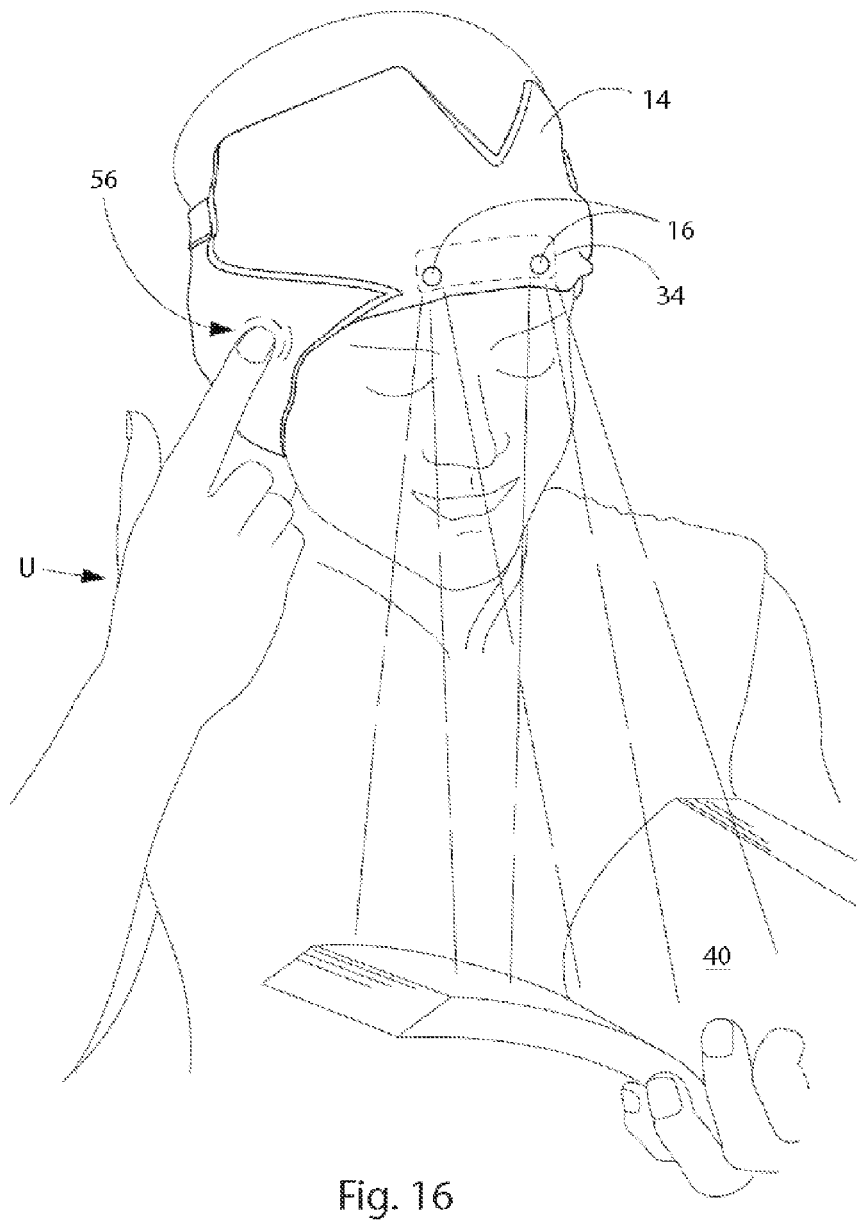

Referring now to FIG. 16, this figure is a view of a user U wearing the device 10 with the eye mask 14 raised and turning the reading light 16 on. As can be seen, the user's U finger is proximal to the on-off switch unit 56 located within the hair wrap 12. After depressing the on-off switch 30, the reading lights 16 are illuminated, shining on the book.

Figure 17:
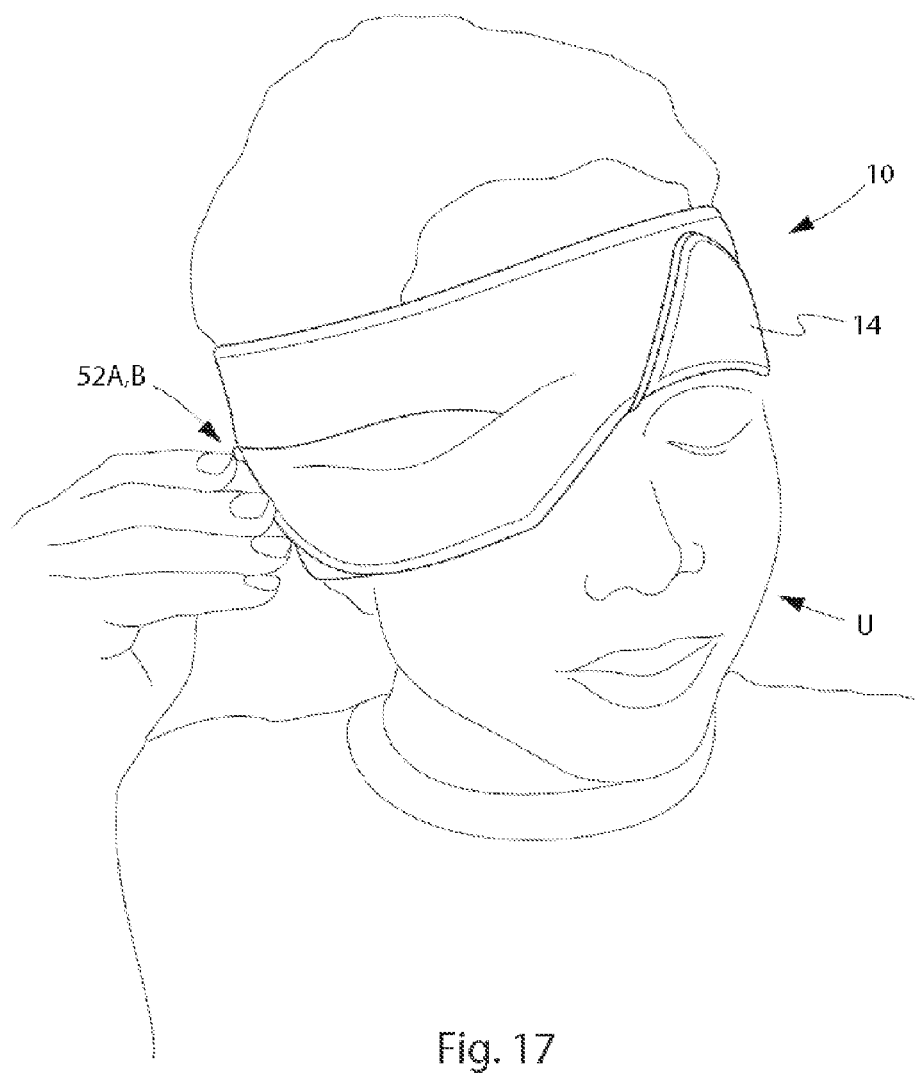
FIG. 17 is a view of a user wearing the invention and preparing to lower the eye mask.

Referring now to FIG. 17, this figure is a view of a user U wearing the device 10 and preparing to lower the eye mask 14. When the user U has decided to go to sleep, the user U has extinguished the reading lights 16 using the on-off switch 30. The user can release the ends of the eye mask 14 from the hair wrap 12 by disengaging the securing means 52A, 52B, thus allowing the eye mask 14 to be lowered from the raised position proximal to the user's U forehead to the lowered position covering the user's U eyes.

Figure 18:
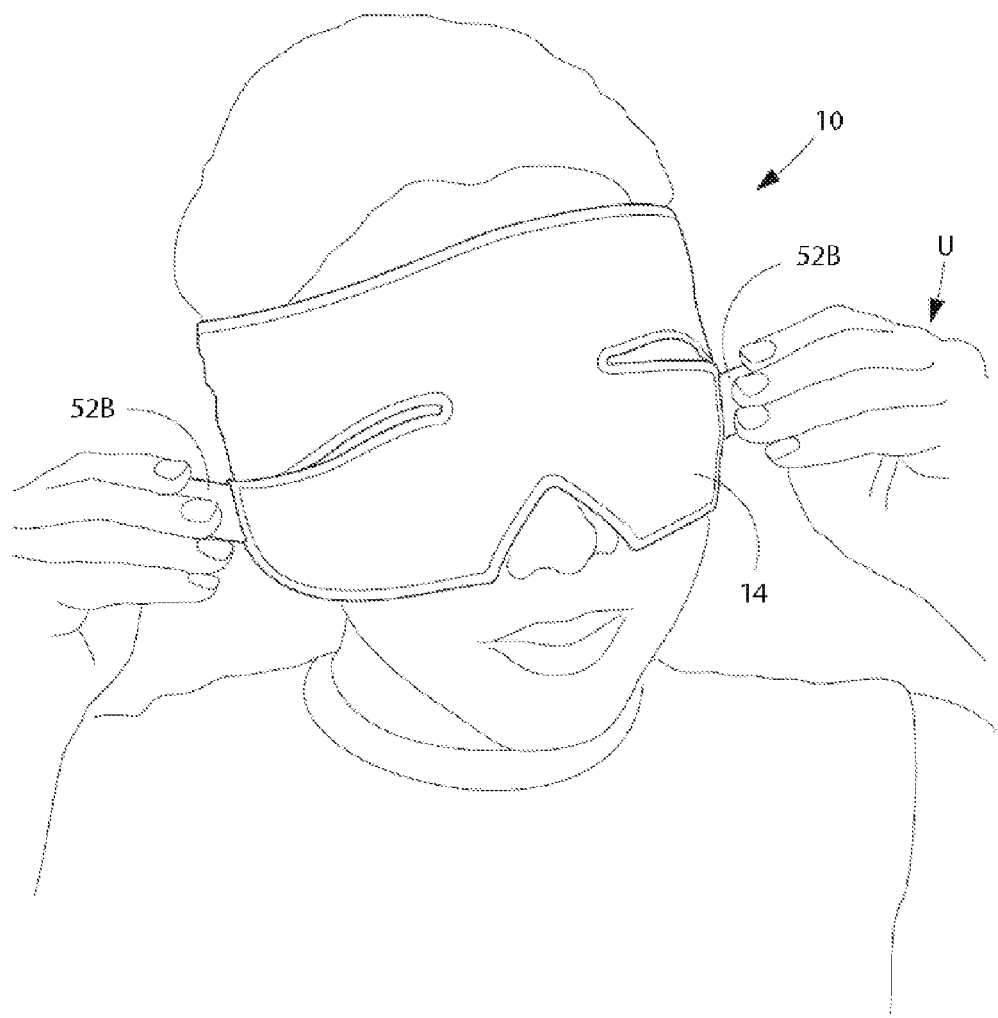
FIG. 18 is a view of a user wearing the invention and lowering the eye mask.

Referring now to FIG. 18, this figure is a view of a user U wearing the device 10 and lowering the eye mask 14 and securing it in place. When the eye mask 14 is in the desired position lowered over the user's eyes, the user U can reconnect securing means 52A, 52B to hold the eye mask 14 in the lowered position, and snugly over the user's U eyes.

Figure 19:
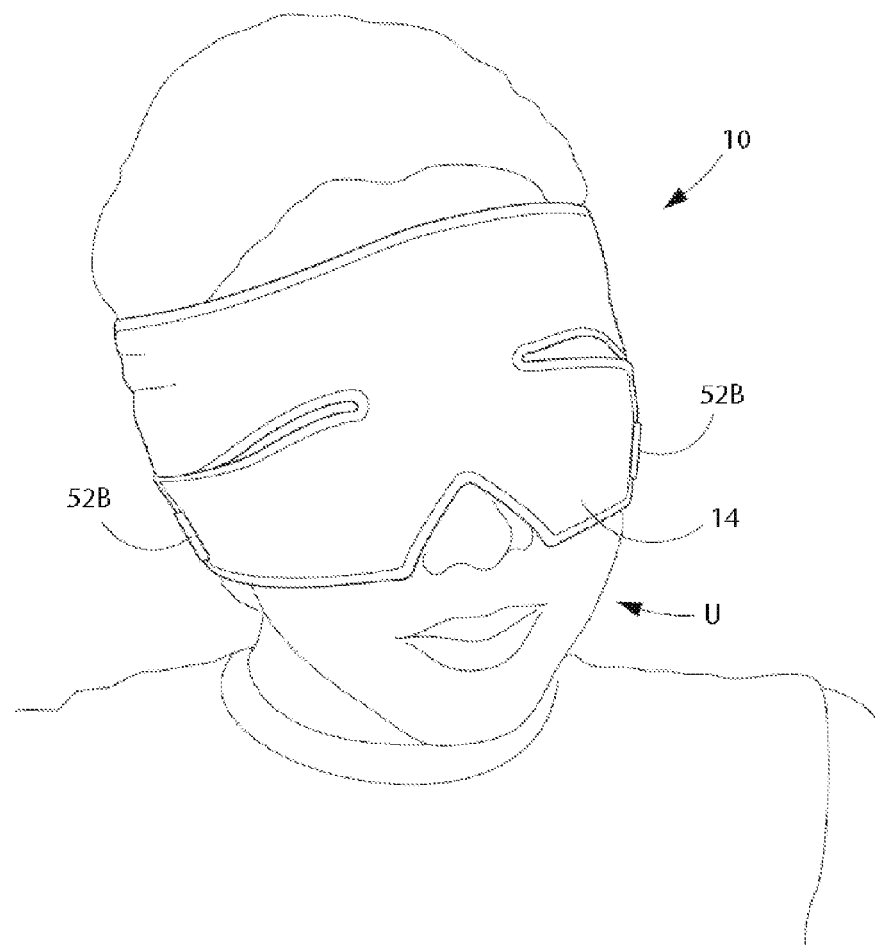
FIG. 19 is a view of a user wearing the invention with the eye mask lowered.

Referring now to FIG. 19, this figure is a view of a user U wearing the device 10 with the eye mask 14 lowered. The user U now can fall asleep without outside light bothering the user U and secure in the knowledge that the user's hair style is being protected from dishevelment if the user U moves while asleep.

Figure 20:
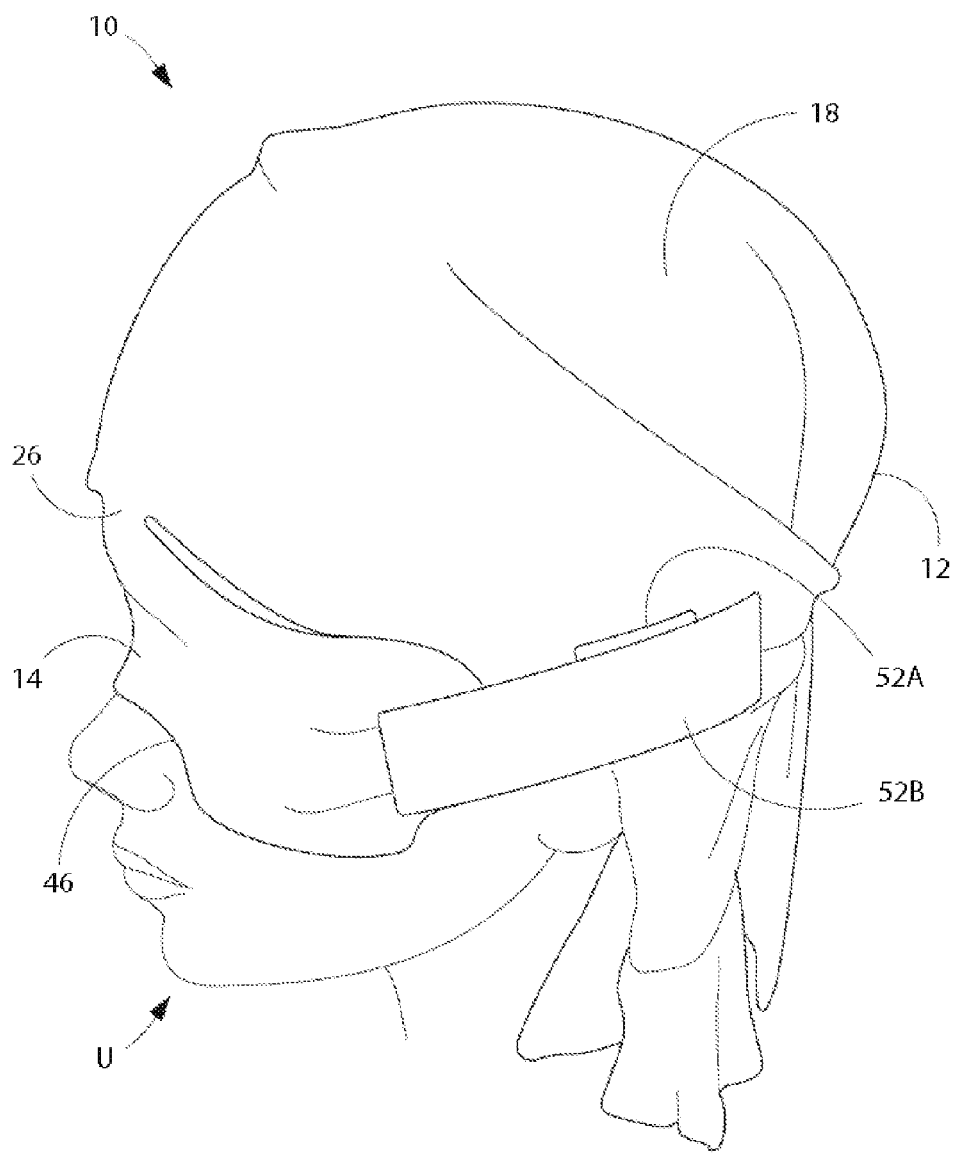
FIG. 20 is a side perspective view of another embodiment of the invention with the eye mask lowered.

Referring now to FIGS. 20-23, these figures show an embodiment in which hair wrap 12 is a sheet of material 18 similar to that shown in FIG. 4 and in which eye mask 14 is a part of the sheet of material 18 and not a separate piece of material. FIG. 20 is a side perspective view of the device 10 with the eye mask 14 lowered. As can be seen, the sheet of material 18 has been draped over the user's U head with the eye mask 14 over the user's U eyes. The sheet of material 18 is has been pulled towards the rear of the user's U head and secured at the rear base of the user's U skull using, for example ties. Exaggerated examples of securing means 52A, 52B are shown securing eye mask 14 to the hair wrap 12 in the lowered position.

Figure 21:
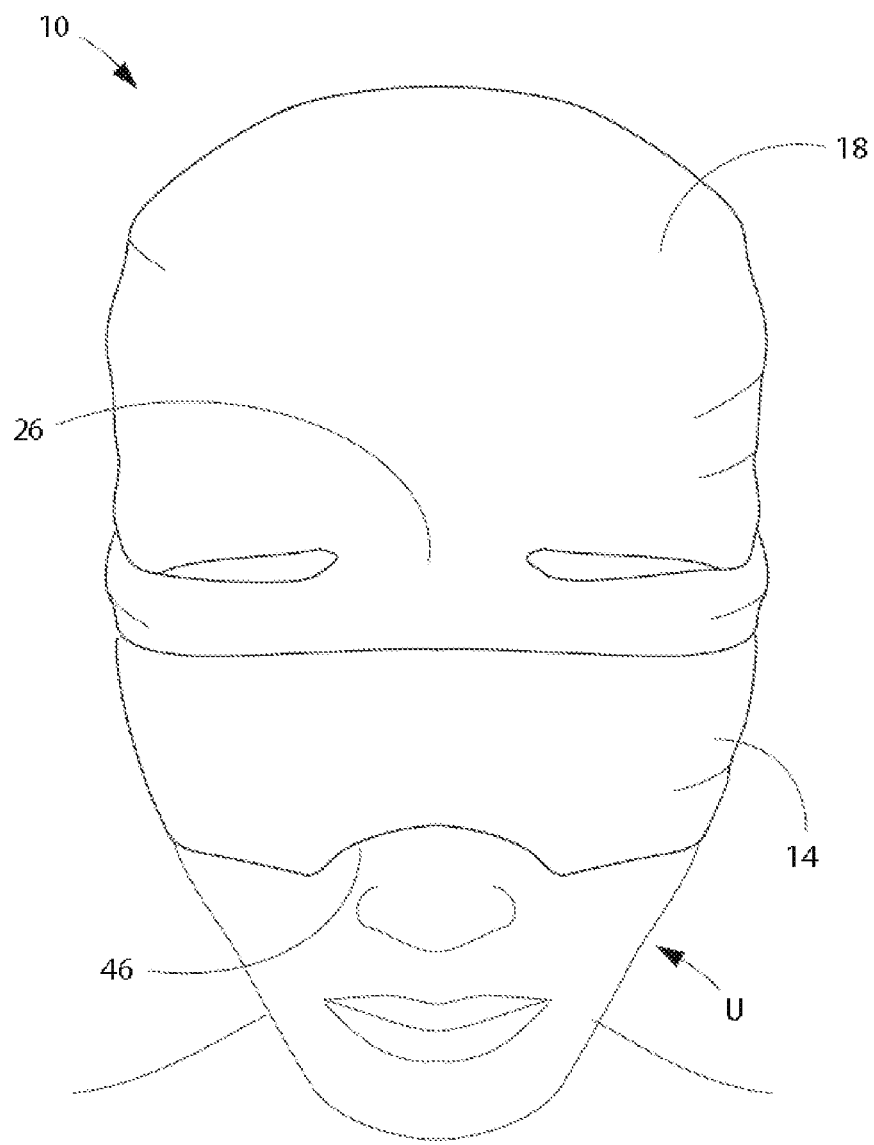
FIG. 21 is a front perspective view of the embodiment of FIG. 20 with the eye mask lowered.

Referring now to FIG. 21, this figure is a front perspective view of the device 10 with the eye mask 14 lowered. Hinge 26 can be seen more clearly.

Figure 22:
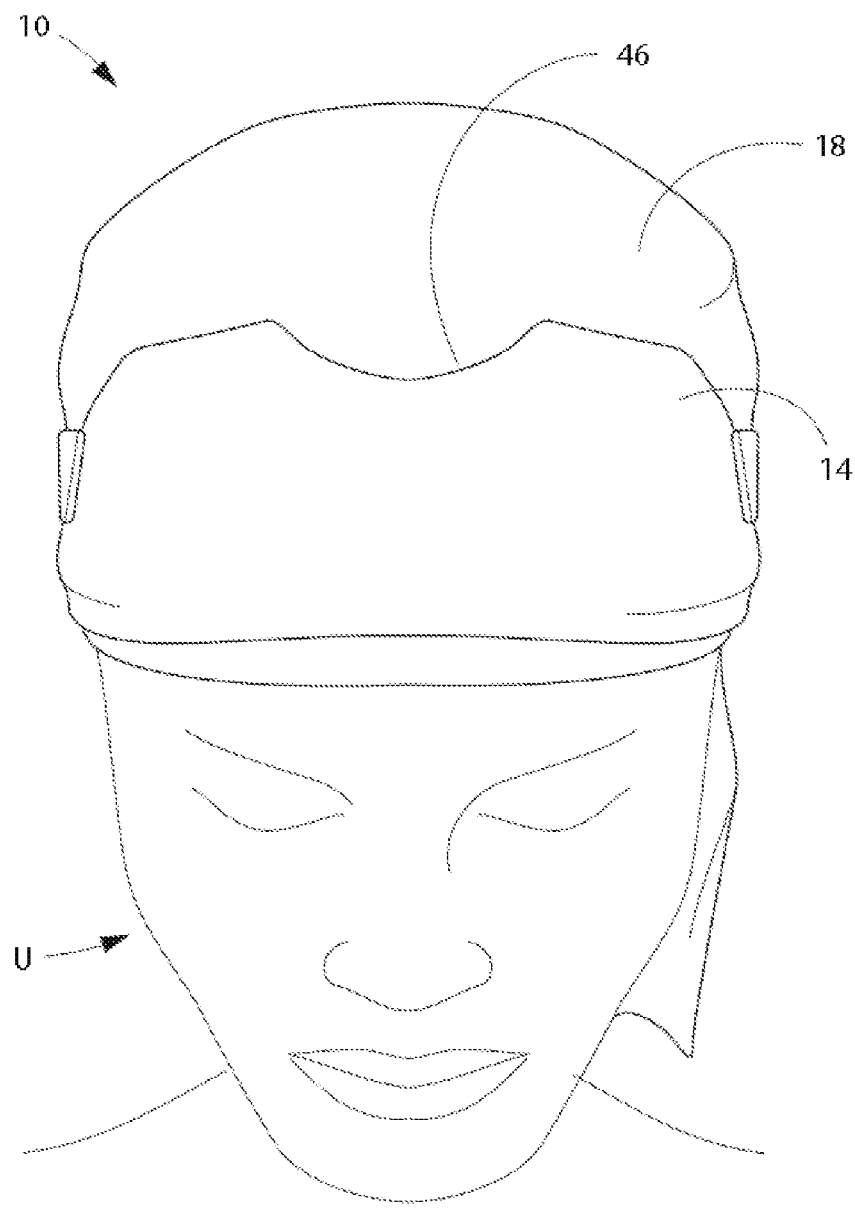
FIG. 22 is a front perspective view of the embodiment of FIG. 20 with the eye mask raised.

Referring now to FIG. 22, this figure is a front perspective view of the device 10 with the eye mask 14 raised. Eye mask 14 is folded upwards so as to be proximal to the user's U forehead, and is secured in this raised position by reconnecting securing means 52A, 52B to the hair wrap 12.

Figure 23:
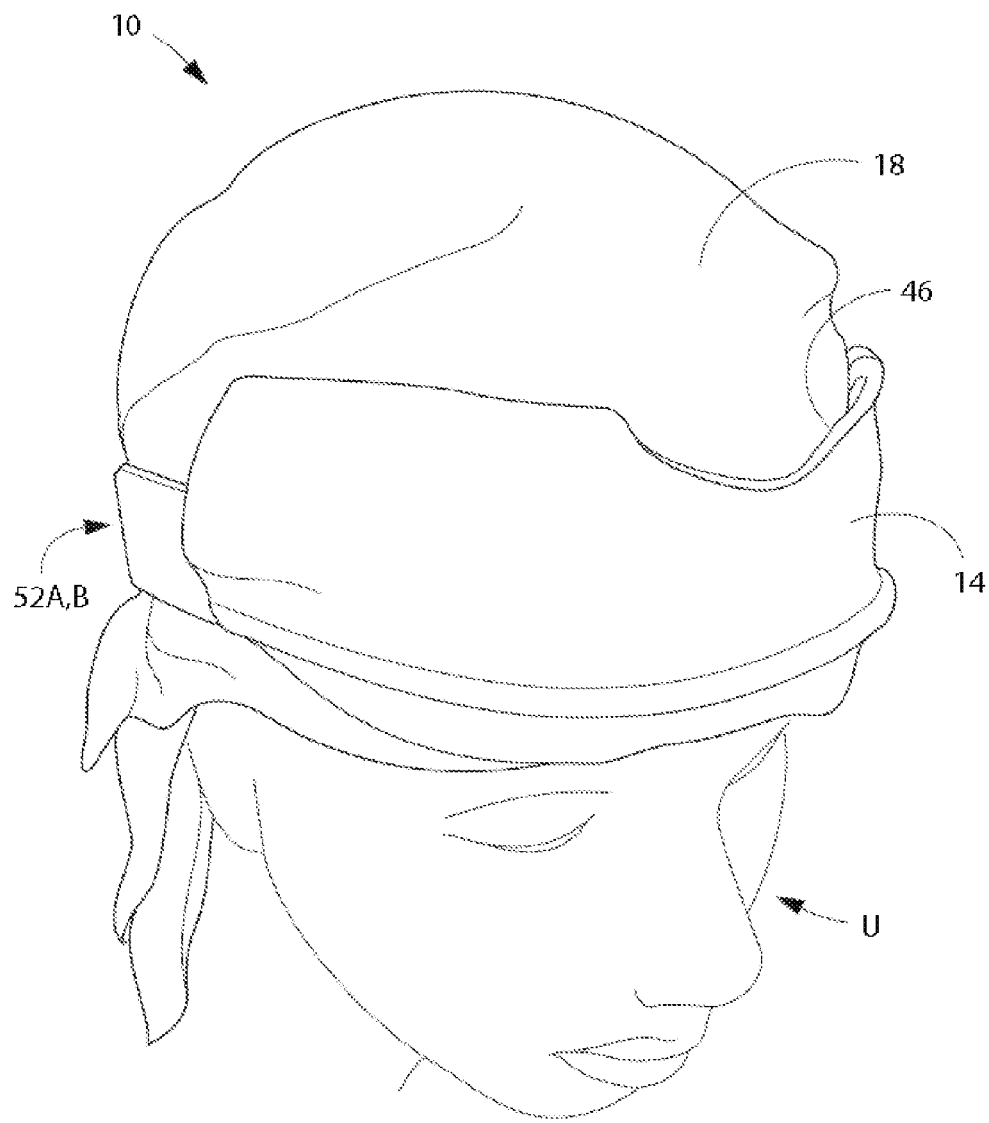
FIG. 23 is a side perspective view of the embodiment of FIG. 20 with the eye mask raised.

Referring now to FIG. 23, this figure is a side perspective view of the device 10 with the eye mask 14 raised showing in more detail the positioning of the raised eye mask 12 and the securing means 52A, 52B.

Figure 24:
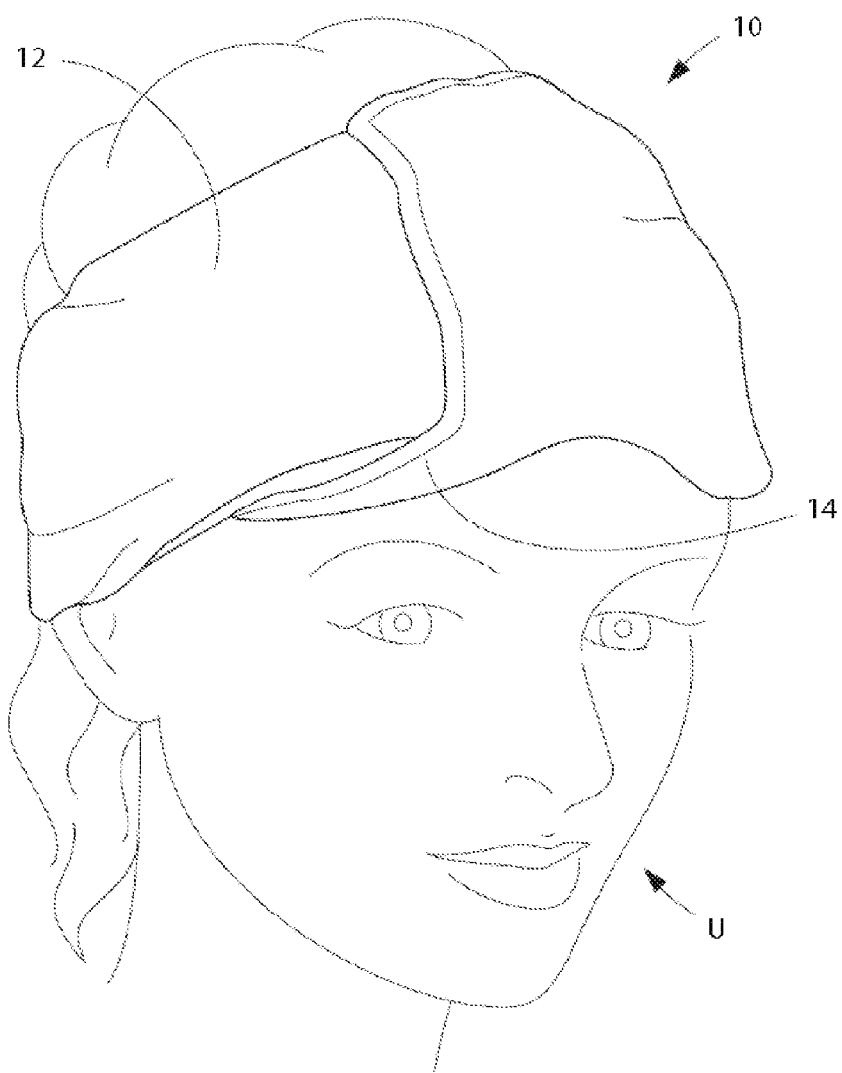
FIG. 24 is a front perspective view of another embodiment of the invention with the eye mask raised in a position tucked under the hair wrap component of the invention.
Figure 25:
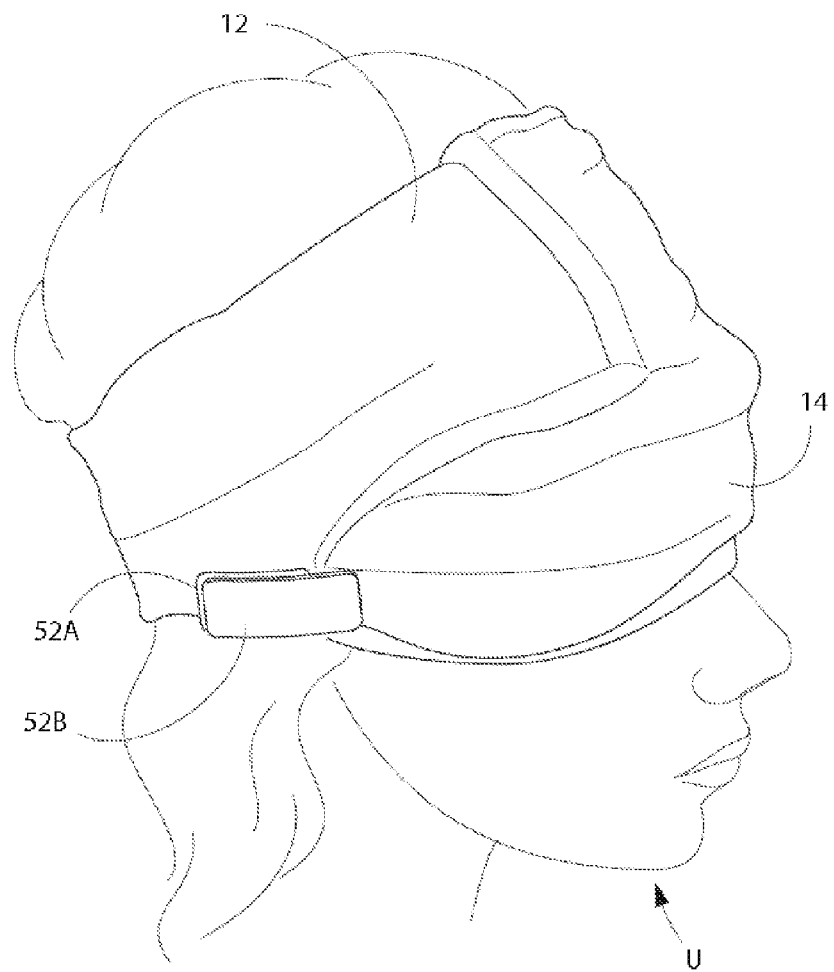
FIG. 25 is a side perspective view of the embodiment of FIG. 25 with the eye mask lowered.

Referring now to FIGS. 24 and 25, these figures show an embodiment of the device 10 in which hair wrap 12 has a head band structure. FIG. 24 is a front perspective view of the device 10 with the eye mask 14 raised in a position tucked under the hair wrap 12 and in which the eye mask 14 is stored in the raised position in a position tucked under the front of hair wrap 12 and generally directly against the user's U forehead.

Referring now to FIG. 25, this figure is a side perspective view of the device with the eye mask 14 lowered. In this embodiment, eye mask 14 does not have a nose cutout. This figure also shows in more detail the positioning of the securing means 52A, 52B.

Figure 26:
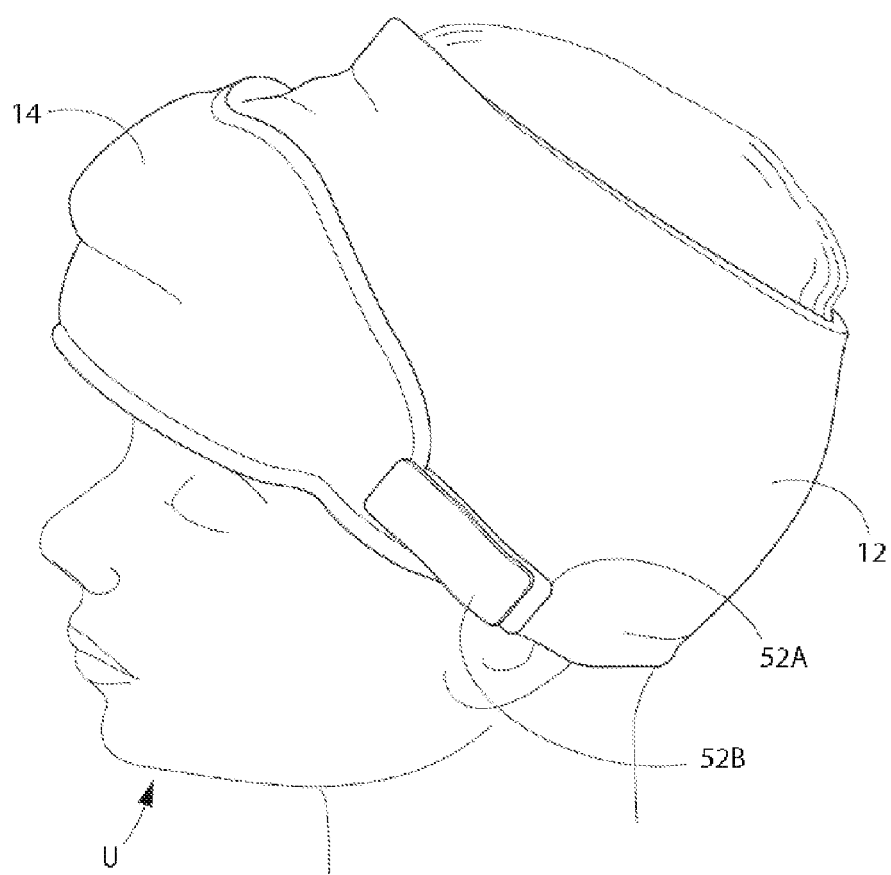
FIG. 26 is a side perspective view of another embodiment of the invention with the eye mask raised.
Figure 27:
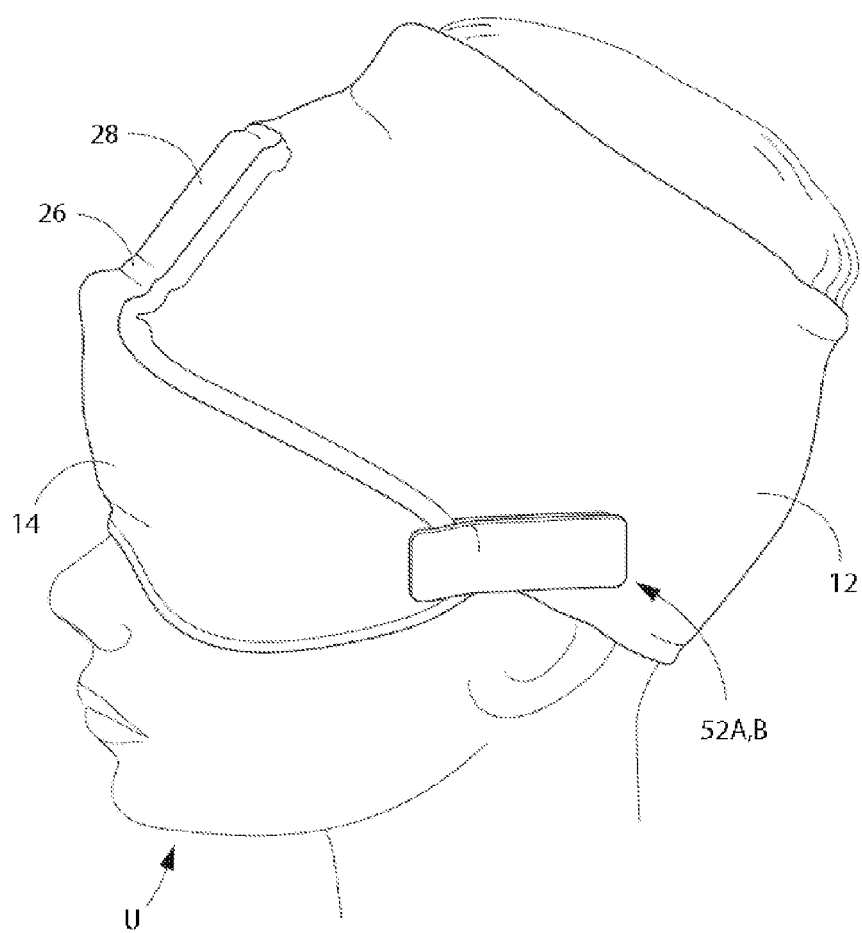
FIG. 27 is a side perspective view of the embodiment of FIG. 26 with the eye mask lowered.

Referring now to FIGS. 26 and 27, these figures show an embodiment of the device 10 in which hair wrap 12 is a head band and in which the eye mask 14 slides upwards and downwards rather than being folded upwards and downwards. FIG. 26 is a side perspective view of the device 10 with the eye mask 14 raised and in which the eye mask 14 is stored in the raised position by generally rotating the eye mask 14 upwards from the lowered position over the user's U eyes to the raised position in front of the hair wrap 12 over the user's U forehead.

Referring now to FIG. 27, this figure is a side perspective view of the device 10 with the eye mask 14 lowered. This figure also shows in more detail the positioning of the securing means 52A, 52B.

Figure 28:
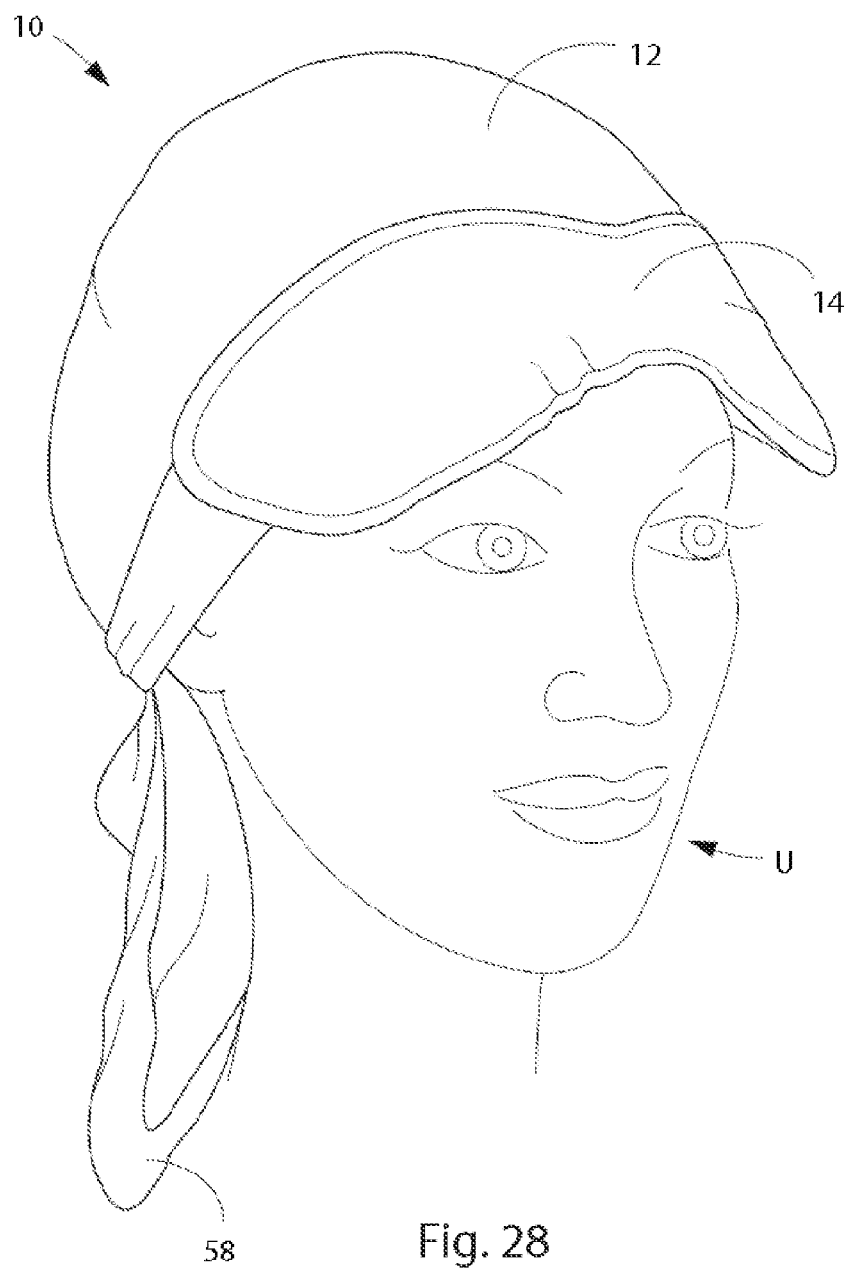
FIG. 28 is a front perspective view of another embodiment of the invention with the eye mask raised in a visor-like configuration.
Figure 29:
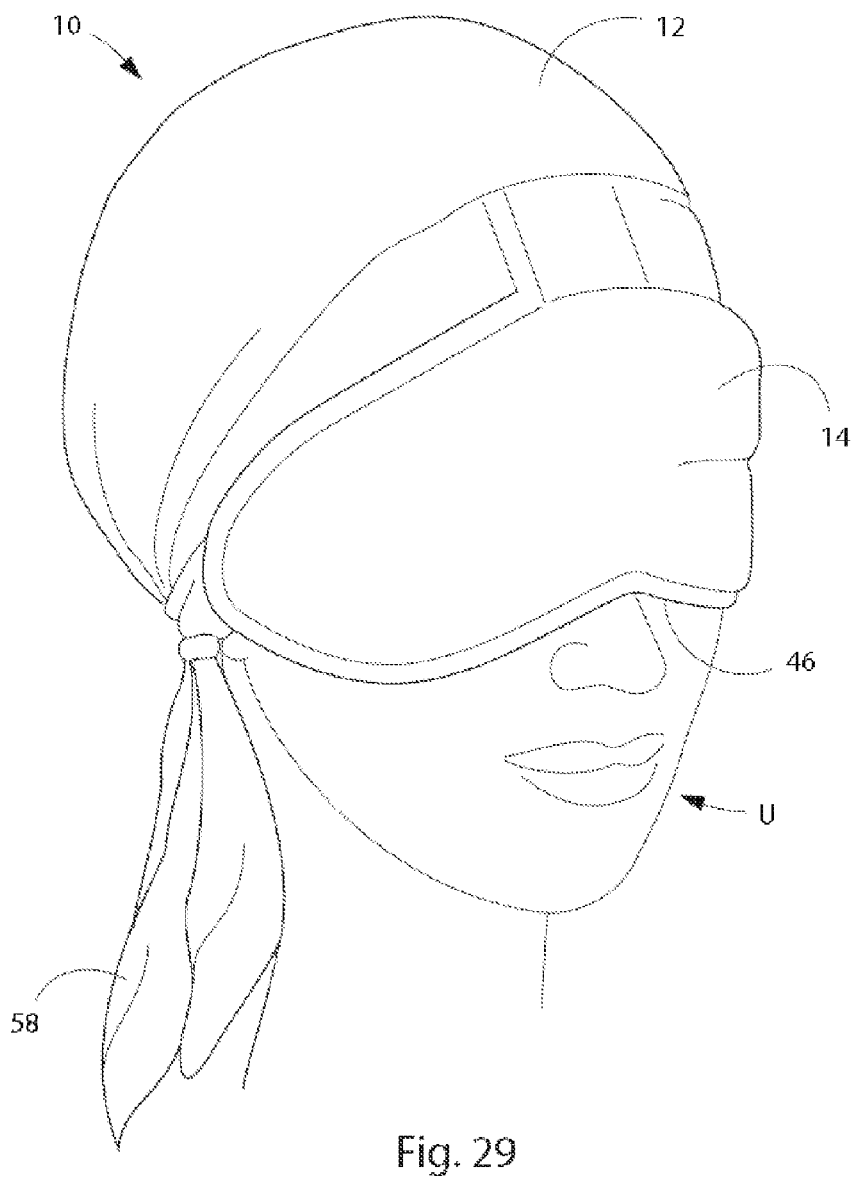
FIG. 29 is a front perspective view of the embodiment of FIG. 28 with the eye mask lowered.

Referring now to FIGS. 28 and 29, these figures show an embodiment of the device 10 in which hair wrap 12 is a sheet of material 18 and in which the eye mask 14 is in the form of an eye shade or visor. In this embodiment, eye mask 14 is stored in a position that emulates an eye shade or visor, and can be considered an embodiment for wearing in public. FIG. 28 is a front perspective view of the device 10 with the eye mask 14 raised in a visor-like configuration. While visor-like eye mask 14 performs the same function in the same manner as other eye masks 14 disclosed herein, the eye mask 14 shown in FIGS. 28 and 29 may provide a more aesthetically pleasing structure to many users U.

Referring now to FIG. 29, this figure is a front perspective view of the device 10 with the eye mask 14 lowered. In this embodiment, eye mask 14 is pulled downwards over the user's U eyes and is secured in position by securing means 52A, 52B. The embodiment in FIGS. 28 and 29 also can comprise an alternative means of securing the hair wrap to the user's head, namely, by tying ends 58 of the sheet of material 18 behind the user's U head at the base of the skull. A knot or another type of fastener, such as a ring or clip, can be used to secure the ends 58 together.

Figure 30:
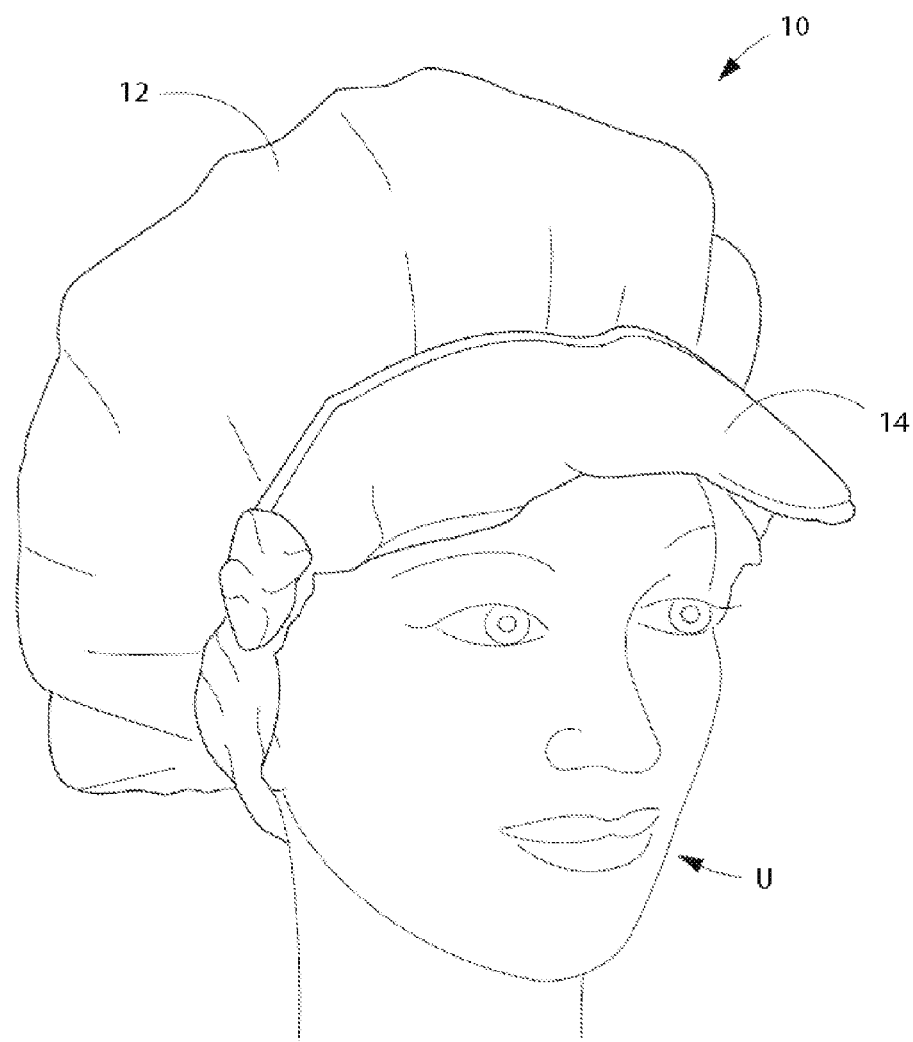
FIG. 30 is a front perspective view of another embodiment of the invention with added volume for use with hair curlers with the eye mask raised.
Figure 31:
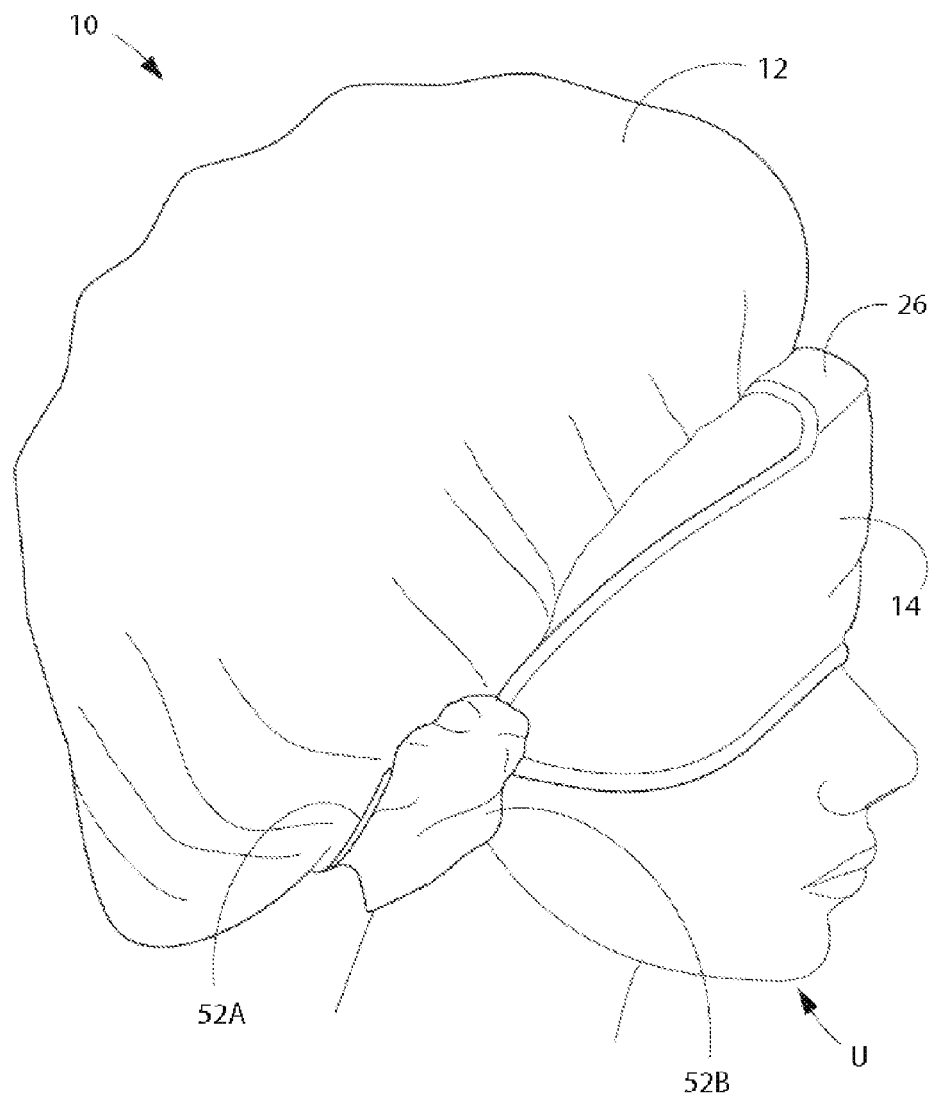
FIG. 31 is a front perspective view of the embodiment of FIG. 30 with the eye mask lowered.

Referring now to FIGS. 30 and 31, these figures show an embodiment of the device 10 in which hair wrap 12 is a more stylized sheet of material 18 and in which the eye mask 14 is in the form of an eye shade or visor. In this embodiment, eye mask 14 is stored in a position that emulates an eye shade or visor, and also can be considered an embodiment for wearing in public. FIG. 30 is a front perspective view of the device 10 with the eye mask 14 raised in a visor-like configuration. While visor-like eye mask 14 performs the same function in the same manner as other eye masks 14 disclosed herein, the eye mask 14 shown in FIGS. 30 and 31 also may provide a more aesthetically pleasing structure to many users U.

Referring now to FIG. 31, this figure is a front perspective view of the device 10 with the eye mask 14 lowered. In this embodiment, eye mask 14 is pulled downwards over the user's U eyes and is secured in position by securing means 52A, 52B. The embodiment in FIGS. 30 and 31 also can comprise an alternative means of securing the hair wrap to the user's U head, such as by elastic located on or in the perimeter of the hair wrap 12. The device 10 can be stretched over the user's U head, and then the elastic is allowed to return to its unstretched state so as to secure the device 10 on the user's U head.

Figure 32:
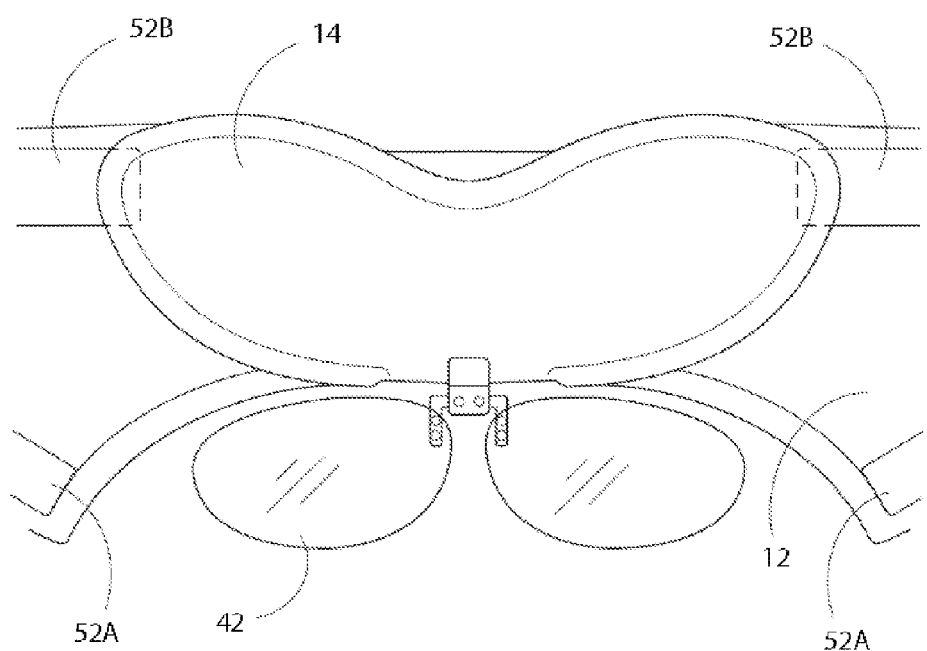
FIG. 32 is a front view of an embodiment of the invention with an eye mask and optional sunglasses or ultraviolet protection lenses.

Referring now to FIG. 32, this figure is a front view of an embodiment of the invention with an eye mask 14 and optional lenses 42, such as sunglasses or ultraviolet protection lenses. Lenses 42 can be the clip on type, and can be used with or without an eye mask 14 attached to the hair wrap.

The material of manufacture of the hair wrap 12 and eye mask 14 can be any fabric material, including, for example, cotton, cotton blends, nylon, polyester, polyester blends, silk, satin, wool, wool blends, leather and other hides, and other natural or synthetic materials or blends thereof. The hair wrap 12 and eye mask 14 can have a filler material, which can be a foam padding, natural or synthetic batting materials or blends thereof, or other natural or synthetic materials or blends thereof. The filler material can be absorbent if it is desired for the device 10 to assist in drying newly styled or washed hair.

The hair wrap 12 can have elastic material embedded in the hair wrap 12 to create one size fits most heads structure and/or to ensure that the hair wrap fits snugly and remains on the user's U head during sleep or other activities.

The battery can be of the replaceable or permanent type. If of the permanent type, it is preferable to have means for recharging the battery. Although the device 10 can be constructed to run off of alternating current (AC), this is not preferred as this would limit the portability of the device 10 and would involve additional wires and safety considerations.

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

What is claimed is:

1. A headgear device that is configured to be rotatable 180 degrees around a user's head from a forward orientation to a backward orientation, the headgear device comprising:
   a hair wrap component configured to maintain at least a portion of a user's hair in a desired position, the hair wrap component structured as a headband, defining a front section and an antipodal rear section, for covering a user's forehead, back-of-the-head, and sides-of-the-head, the front section having a smaller band width than the rear section such that the front section is configured to contour about a user's face, in the forward orientation on the user's forehead, and such that the front section is configured to contour about a user's neck, in the backward orientation on the user's back-of-the-head;
   an eye mask component attached to the front section of the hair wrap component via a fabric connection hinge, the eye mask component defining a nose cut-out opposite the fabric connection hinge, the eye mask component configured to fold upwards, about the fabric connection hinge, to a raised position against the hair wrap component, the eye mask component also configured to unfold downwards about the fabric connection hinge, to a lowered position, so as to contour about a user's eyes when the hair wrap component is in the forward orientation on the user's forehead, and the eye mask component also configured to unfold downwards about the fabric connection hinge, to the lowered position, so as to partially cover a user's neck when the hair wrap component is in the backward orientation on the user's back-of-the-head; and
   a securing means configured to secure the eye mask component in each of the lowered position and the raised position;
   wherein, when the hair wrap component is in the forward orientation on the user's forehead, and when the eye mask component is unfolded downwards about the fabric connection hinge to the lowered position, the nose cut-out of the eye mask component is configured to contour about a user's nose.

2. The headgear device as claimed in claim 1, wherein the eye mask component further comprises a light component, and further comprises an on-off switch and a power source, wherein the light component, the on-off switch, and the power source are in electrical communication with each other.

3. The headgear device as claimed in claim 2, wherein the hair wrap component further comprises the power source and the on-off switch.

* * * * *